United States Patent [19]
Romeo et al.

[11] Patent Number: 5,795,869
[45] Date of Patent: Aug. 18, 1998

[54] SULFATED LYSO-GANGLIOSIDE DERIVATIVES

[75] Inventors: Aurelio Romeo, Rome; Gunter Kirschner, Abano Terme; Carlo Chizzolini, Padua, all of Italy; Hari Manev, Pittsburgh, Pa.; Laura Facci, Vicenza, Italy

[73] Assignee: Fidia S.p.A., Abano Terme, Italy

[21] Appl. No.: 530,267

[22] PCT Filed: Mar. 4, 1994

[86] PCT No.: PCT/US94/01966

§ 371 Date: Nov. 2, 1995

§ 102(e) Date: Nov. 2, 1995

[87] PCT Pub. No.: WO94/20516

PCT Pub. Date: Sep. 15, 1994

[30] Foreign Application Priority Data

Mar. 4, 1993 [IT] Italy ................... PD93A0044

[51] Int. Cl.$^6$ ............... A61K 31/70; C07H 15/00
[52] U.S. Cl. ............... 514/25; 514/54; 536/4.1; 536/53; 536/54; 536/55; 536/55.3; 536/124
[58] Field of Search ............... 514/25, 54; 536/4.1, 536/53, 54, 55, 55.3, 124

[56] References Cited

U.S. PATENT DOCUMENTS 5,350,841 9/1994 Romeo et al. ............... 536/53

OTHER PUBLICATIONS

Olney *Annu. Rev. Pharmacol. Toxicol.* 1990, 30, 47–71.

Greene *Scientific American* 1993, 269(3), 99–105.

Fauci *Proc. Natl. Acad. Sci. USA* Dec. 1986, 83(24), 9278–9283.

Handa et al. *Biochem. Biophys. Res. Commun.* Feb. 28, 1991, 175(1), 1–9.

*Primary Examiner*—Kathleen K. Fonda
*Attorney, Agent, or Firm*—Birch, Stewart, Kolasch & Birch, LLP

[57] ABSTRACT

Semisynthetic analogues of gangliosides selected from the group consisting of N-sulfo-, N-hydrocarbyl-sulfonyl- and N-hydrocarbyloxy-sulfonyl-N,N'-dilyso-gangliosides and the N'-acyl derivatives thereof, N'-sulfo-, N'-hydrocarbylsulfonyl- and N'-hydrocarbyloxy-sulfonyl-N, N'-dilyso-gangliosides and the N-acyl derivatives thereof, N,N'-di or polysulfo-N,N'-di- or poly-lyso-gangliosides, N,N'-di- or polyhydrocarbylsulfonyl-N,N'-di- or poly-lyso-gangliosides and N,N'-di- or polyhydrocarbyloxy-N,N'-di- or poly-lyso-gangliosides, and functional derivatives thereof, and salts of these compounds, have protective activity against neurotoxicity induced by excitatory amino acids and are foreseen to be used in therapy in the nervous system and in modulating of the expression of determinants such as $CD_4$ on the surface of human cells in the immune system.

37 Claims, No Drawings

SULFATED LYSO-GANGLIOSIDE DERIVATIVES

This is the U.S. National stage entry under 35 U.S.C. 371 of PCT/US94/01966, filed Mar. 4, 1994.

OBJECT OF THE INVENTION

The present invention concerns novel semisynthetic ganglioside analogues, and more precisely N-sulfo-, N-hydrocarbylsulfonyl- and N-hydrocarbyloxysulfonyl-N, N'-dilyso-gangliosides and the N'-acyl derivatives thereof, N'-sulfo-, N'-hydrocarbylsulfonyl- and N'-hydrocarbyloxysulfonyl-N,N'-dilyso-gangliosides and the N-acyl derivatives thereof, N,N'-di or polysulfo-N,N'-di- or poly-lyso-gangliosides, N,N'-di or polyhydrocarbylsulfonyl-N,N'-di or poly-lyso-gangliosides and N,N'-di- or polyhydrocarbyloxysulfonyl-N,N'-di or polylyso-gangliosides and the functional derivatives thereof, and salts of all these compounds.

The novel derivatives have interesting pharmacological properties, especially protective activity against neurotoxicity induced by excitatory amino acids, such as glutamic acid, and can therefore be used in therapy for the nervous system, such as for conditions following degeneration or lesions, i.e., ischemia, hypoxia, epilepsy, trauma and compression, metabolic dysfunction, aging, toxic-infective diseases and chronic neurodegeneration, such as Alzheimer's disease, Parkinson's disease or Huntington's chorea.

The novel compounds of the invention, thanks to their neuritogenic activity, can be used to advantage in therapies aimed at nervous function recovery, such as in peripheral neuropathies and pathologies associated with neuronal damage.

Moreover, the novel derivatives which are object of the present invention have valuable properties for the modulation of the expression of specific determinants, such as $CD_4$, present on the surface of human cells belonging to the immune system.

The ability of the above compounds to modulate expression of the molecule $CD_4$, a membrane glycoprotein expressed in various cell types such as thymocytes, lymphocytes, monocytes and macrophages has great applicative potential in a wide range of human pathologies.

Compounds of the present invention may have therapeutic use in all situations wherein it is necessary to prevent and/or treat infections involving $CD_{4+}$ cells, such as infections the etiological agents whereof are microorganisms belonging to the human immunodeficiency (HIV) family of viruses. Moreover, the modulation of $CD_4$ is useful in systemic or organ-specific autoimmune diseases, such as multiple sclerosis, rheumatoid arthritis, chronic polyarthritis, lupus erythematosus, diabetes mellitus, and also to prevent the phenomenon of organ transplant rejection as well as rejection by the transplanted material against the host, as in the case of bone marrow transplant, and in all cases where the desired effect is to obtain tolerance towards "self" and "non-self" antigens.

Functional derivatives of the abovesaid semisynthetic ganglioside analogues are for example esters and amides of the carboxyl groups of sialic acid residues and may also be inner esters with lactone bonds between their sialic carboxyl groups and hydroxyl groups in the oligosaccharide, analogous to those known in the case of gangliosides, and possibly also the derivatives of all these compounds, in which the hydroxyl groups are esterified with organic acids or sulfuric acid.

Of particular interest are the esters with organic acids wherein all the hydroxyl groups, both those of the saccharide component and the free groups of sialic acid, and the hydroxyl group of the ceramide residue are esterified, that is "peracylated" and also the persulfated derivatives, i.e. those wherein all the hydroxyl groups are esterified with sulfuric acid.

The term "N,N'-dilyso-ganglioside" in the aforesaid definition means a ganglioside from which both the acyl group on the amino group in its ceramide residue, and the acyl group(s) of its sialic acid residue(s) have been removed. In the new compounds of the invention the ceramide amino group (position N) or all the amino groups of sialic acid (a position which is collectively called N' for brevity), or both the free amino functions of N,N'-dilyso-gangliosides are therefore acylated with the above-mentioned radicals.

The term "-di-" therefore refers to positions N and N' in the sense defined above and not to the actual number of deacylated amino functions.

In the expressions N'-sulfo, N'-hydrocarbyloxy-sulfonyl and N'-hydrocarbylsulfonyl-N,N'-dilyso-gangliosides the substituents in position N' are equal in number to the neuraminic acids present in the ganglioside. Therefore, the definition "di-" or "poly-" has been chosen for the possible substituents in this position.

As explained below, the two groups substituting the N and N' amino groups may be different, thus leading to "unsymmetrical" compounds.

In the substituted derivatives in just one of the positions N and N', with one of the sulfured radicals indicated previously, the other amino group may be substituted with an acyl group of an organic acid.

In the illustrative examples and also elsewhere the expression "-lyso" without any indication of the position, as in the literature, should be taken to mean the position of the ceramide amino group.

The salts can be metal salts of the free carboxyl groups, for example the sialic carboxyl groups or carboxyl groups possibly present in the acyl residues of the acyl amido groups, as for example when the acyl group is derived from a polybasic acid, such as succinic acid; moreover the salts may be derived from organic bases, especially from those which are therapeutically acceptable. In addition, metal salts or those with organic bases on any sulfate groups which may be present may be mentioned.

Another aspect of the invention is directed to salts with acids at amino groups which may be present, for example at the amino group of a N-hydrocarbyl-sulfonyl-N,N'-dilyso-ganglioside. In this case too the salts of acids which can be used in therapy are preferred. Also included in the invention are salts deriving from metals, bases or acids not normally used in therapy and such salts may possibly be used for the purification of the new products.

The aforesaid semisynthetic ganglioside analogues are novel.

Another aspect of the invention is directed to the use of these novel compounds in therapy, especially to treat the abovementioned disorders affecting the central or peripheral nervous systems or the immune system. Moreover, the invention is directed to pharmaceutical preparations containing one or more of the novel compounds, possibly together with a pharmaceutical excipient or vehicle.

The term "hydrocarbyl" as used alone or as a part of a hydrocarbyloxy moiety in the abovesaid definition of the new compounds indicates the monovalent residue of a substituted or unsubstituted, saturated or unsaturated hydrocarbon, i.e. the radical obtained from the formula of a hydrocarbon by elimination of a hydrogen atom, and such radicals are therefore, for example, alkyl, aryl, aralkyl or cycloalkyl. The alkyl groups have preferably a maximum of 24 carbon atoms and are preferably $C_{1-6}$ alkyls, especially methyl, ethyl, propyl, isopropyl, n-butyl, isobutyl or n-pentyl or trimethylmethyl. An aryl radical has preferably a maximum of 12 carbon atoms and is preferably a phenyl group, possibly substituted with 1–3 $C_{1-4}$ alkyl groups or $C_{1-4}$ alkoxy groups, especially methyl or methoxy groups. An aralkyl group has preferably a maximum of 12 carbon atoms, the aliphatic part being preferably a $C_{2-4}$ alkylene group, and the aromatic part is the same group already indicated as preferential for the aromatic groups.

Cycloalkyl is preferably a radical deriving from cyclopropane, cyclobutane, cyclopentane or cyclohexane, or from one of their homologues substituted with $C_{1-4}$ alkyl groups, for example methyl groups.

The hydrocarbyl groups can also be substituted with functions, especially by hydroxyl or amino groups or halogens, for example chlorine or bromine atoms. Moreover, the hydrocarbyl groups may also be interrupted in the carbon atom chain by heteroatoms, such as especially by nitrogen atoms or —NH— groups, respectively. Unsaturated hydrocarbyl groups are especially those deriving from long-chained alkyl groups, for example $C_{14-22}$ alkenyl groups. The saturated alkyl radicals with the same number of carbon atoms are also interesting.

Among the hydrocarbyl radicals of the aromatic series, special mention should be made of the phenyl variety with a maximum of 12 carbon atoms, for example the unsubstituted phenyl radical or a phenyl radical substituted with between 1 and 3 substituents selected from the group consisting of $C_{1-4}$ alkyl groups and $C_{1-4}$ alkoxy groups, especially methyl and methoxy groups, amino groups and halogens such as chloro or bromo.

Araliphatic radicals, i.e. aralkyl radicals, are preferably those with the same aromatic groups as those illustrated above for the aromatics, and with a $C_{2-4}$ alkylene radical in the aliphatic part.

Cycloalkyl hydrocarbyl radicals are preferably those with one single ring and with a maximum of 10 carbon atoms, especially cyclopropyl, cyclobutyl, cyclopentyl, cyclohexyl and their derivatives substituted with between 1 and 3 $C_{1-4}$ alkyl groups, especially methyl groups.

The carbon atom chain may be interrupted by heteroatom links thus leading to heterocyclic radicals such as pyridyl.

In the novel compounds of the present invention, wherein, besides Et sulphurated group in one of the positions N or N', there is an acyl group in the other, the acyl group may be for example one of the groups present in natural gangliosides, i.e. an acyl deriving from a saturated or unsaturated fatty acid with between 16 and 22 carbon atoms or from a corresponding hydroxy acid, as far as the amino group of the ceramide residue is concerned, and an acyl deriving from acetic or glycolic acid with regard to the amino group or the amino groups of the neuraminic residue.

Also coming within the scope of the present invention are mixtures of the aforesaid chemical compounds, and in particular the derivatives of natural gangliosides obtainable by extraction from tissues of the nervous system or by enzymatic reactions, where the acyl groups are mixtures of acyl groups from higher aliphatic acids present at the sphingosine nitrogen atom and mixtures of acyl groups from acetic or glycolic acid at the neuraminic nitrogen and, wherein, possibly, hydroxy groups of the sialic acids are in esterified form.

The acyl groups present in position N or N' may derive from aliphatic acids and have preferably a maximum of 24 carbon atoms, especially those which have between 12 and 16 carbon atoms and are straight-chained, or those having between 1 and 11 carbon atoms and a straight or branched chain, such as formic acid, acetic acid, propionic acid, butyric acids, valeric acids, especially n-valeric acid, isovaleric acid, trimethyl-acetic acid, caproic acid, isocaproic acid, heptanoic acid, octanoic acid, pelargonic acid, capric acid, undecanoic acid, di-tertbutyl-acetic acid and 2-propyl-valeric acid, as well as lauric, myristic, palmitic, oleic, elaidic and stearic acid.

The acyl radicals may also derive from aliphatic acids substituted with one or more polar substituents, such as halogens, in particular chlorine, bromine and fluorine, free or esterified hydroxy groups, ketone, ketal and acetal groups derived from lower aliphatic or araliphatic alcohols, ketoxy or aldoxy or hydrazone groups, free or esterified mercapto groups with a lower aliphatic or araliphatic acid or etherified with lower aliphatic or araliphlatic alcohols, free or esterified carboxyl groups, free or esterified sulfon groups with lower aliphatic or araliphatic alcohols, sulfamide or sulfamide groups substituted with lower alkyl or aralkyl groups or lower alkyl groups, sulfoxide groups or sulfone groups derived from lower alkyl or aralkyl groups, or lower alkylene groups, nitril groups, free or substituted amino groups, and ammonium derivatives of such amino groups.

The acyl radicals substituting one of the neuraminic or sphingosine amino groups of the new derivatives may also be radicals of an aromatic, araliphatic, cycloaliphatic, aliphatic-cycloaliphatic or heterocyclic acid.

Aromatic acyl groups are mainly those deriving from benzoic acid or its homologues wherein the phenyl residue is substituted with, for example, 1 to 3 $C_{1-4}$ alkyl or $C_{1-4}$ alkoxy groups, especially methyl and methoxy groups and/or by one of said polar groups, for example free or alkylated amino groups.

Araliphatic acyl groups have preferably a $C_{2-4}$ alkylene chain as their aliphatic portion, and the aromatic portion is preferably one of the abovesaid aromatic groups. Cycloaliphatic acyl radicals are preferably those deriving from an alicyclic hydrocarbon with between 3 and 6 carbon atoms in the ring, such as cyclopropane, cyclobutane, cyclopentane and cyclohexane.

Heterocyclic radicals derive preferably from a monocyclic heterocyclic compound with just one heteroatom link, such as —O—, —N=, —NH—, —S—, and may be aromatic or aliphatic by nature, such as acids of the pyridine group, for example nicotinic or isonicotinic acid, the furane group, such as 2-furoic acid, or the thiophene group, such as 2-thiophene-acetic acid, the imidazole group, such as 4-imidazole-acetic acid, or the pyrrole group, such as 1-methyl-2-pyrrole-carboxylic acid.

Functional derivatives of the new semisynthetic ganglioside derivatives according to the present invention are esters, inner esters and amides of the sialic carboxylic groups. The ester groups derive particularly from aliphatic alcohols and especially from those with a maximum of 12 and preferably 6 carbon atoms, or from araliphatic alcohols with preferably one single benzene ring, possibly substituted with 1–3 $C_{1-4}$ alkyl groups, for example methyl groups, with a maximum of 4 carbon atoms in the aliphatic chain, or from alicyclic or aliphatic-alicyclic alcohols with one single cycloaliphatic ring and a maximum of 14 carbon atoms, or from heterocyclic alcohols with a maximum of 12 carbon atoms, and preferably 6, and one single heterocyclic ring containing a heteroatom link chosen from the group formed by —N=, —NH—, —O—, and —S—.

The amido groups of the carboxyl functions derive from ammonia or from amines of any class, preferably with a maximum of 12 carbon atoms. Special mention should be made of lower aliphatic amines, such as methylamine, ethylamine, propylamine, and butylamine.

Said alcohols and amines can then be substituted, especially by functions chosen from the groups formed by hydroxyl, amino, alkoxyl groups with a maximum of 4 carbon atoms in the alkyl moiety, carboxyl or carbalkoxyl with a maximum of 4 atoms in the alkyl moiety, alkylamino or dialkylamino groups with a maximum of 4 carbon atoms in the alkyl group, and they may be saturated or unsaturated, especially with one double bond. The alcohols may be monovalent or polyvalent, particularly bivalent. Of the aliphatic alcohols, special mention should be made of the lower alcohols with a maximum of 6 carbon atoms, such as methyl alcohol, ethyl alcohol, propyl alcohol and isopropyl alcohol, n-butyl alcohol, isobutyl alcohol, tert-butyl alcohol and, of the bivalent alcohols, ethylene glycol and propylene glycol. Of the araliphatic alcohols, special mention should be made of those with just one benzene residue, such as benzyl alcohol and phenethyl alcohol; of the alicyclic alcohols, preference is given to those with just one cycloaliphatic ring, such as cyclohexyl alcohol (cyclohexanol) or terpene alcohols. Among the heterocyclic alcohols, special mention should be made of tetrafuranol and tetrapyranol.

Of the functional derivatives of the novel semisynthetic analogues according to the present invention, special importance should be given to the peracylated derivatives on the hydroxyl groups of the saccharide portion of the sialic acids and ceramide.

In such derivatives the acyl radicals may derive from aliphatic, aromatic, araliphatic, alicyclic or heterocyclic acids, such as those listed above as acylating the N or N' acylamino groups. They are preferably derived from aliphatic acids with a maximum of 10 carbon atoms and preferably 6 carbon atoms, such as formic, propionic, valerianic, butyric, caproic or hexanoic acid. They may also be derived from substituted acids, preferably with the same number of carbon atoms, and particularly substituted with hydroxyl, amino, or carboxyl groups, such as lactic acid, glycine, malonic acid, maleic acid or succinic acid.

Among the acyl groups deriving from aromatic acids, particular mention should be made of those deriving from benzoic acid or its derivatives substituted with methyl, hydroxyl, amino or carboxyl groups, such as p-aminobenzoic acid, salicylic acid or phthalic acid.

Of the esters corresponding to the ganglioside hydroxyls, special consideration should be given to the esters of sulfuric acid, above all those wherein all the OH groups, namely those in the saccharide portion, the ceramide residue and in the sialic acid residues, are sulfated. Such O-persulfated derivatives can be prepared from said semisynthetic analogues by subsequent treatment with the sulfuric acid anhydride-trimethylamine complex, for example in dimethylformamide over a long period of time and at a high temperature.

Using shorter time intervals and/or smaller quantities of reagent it is however also possible to obtain partial esters of the basic ganglioside, and these too form part of the invention. Such partial esters usually represent mixtures with O-sulfated groups in various positions of the ganglioside molecule.

The sulfated compounds are easily transformed into their metal or organic base salts, for example into their alkali metal salts, especially sodium salts, by treatment with bases or basic salts, for example, in the case of sodium salts, with sodium carbonate. Especially for therapeutic applications, the sulfated esters are in the form of such salts, especially sodium salts.

Among the most important basic gangliosides to be used in the preparation of the novel derivatives are for example those wherein the oligosaccharide is formed by a maximum of 4 residues of saccharide, and wherein the saccharide portion is unitary. It is preferable to choose hexoses from the group formed by N-acetylglucosamine and N-acetylgalactosamine. The gangliosides of said group are for example extracted from vertebrate brains, such as those described in the article "Gangliosides of the Nervous System" in "Glycolipid Methodology", Lloyd A., Witting Fd., American Oil Chemists Society, Champaign, III, 187–214 (1976) (see in particular FIG. 1), for example gangliosides GM$_4$, GM$_3$, GM$_2$, GM$_1$-GlcNAC, GD$_2$, GD$_{1a}$-GalNAC, GT$_{1c}$, G$_Q$, GT$_1$, and particularly those wherein the oligosaccharide contains at least one glucose residue or one galactose residue and one N-acetylglucosamine residue or N-acetylgalactosamine residue and above all the following:

GM$_1$

Gal(1→3) GalNAC(1→4) Gal(1→4) Glc(1→1) Ceramide

NANA

GD1a

Gal(1→3) GalNAC(1→4) Gal(1→4) Glc(1→1) Ceramide

 

NANA  NANA

GD$_{1b}$

Gal(1→3) GalNAC(1→4) Gal(1→4) Glc(1→1) Ceramide

NANA

NANA

Gal(1→3) GalNAC(1→4) Gal(1→4) Glc(1→1) Ceramide

 

NANA  NANA

NANA where Glc stands for glucose, GalNAC stands for N-acetylgalactose amine, Gal stands for galactose, NANA stands for N-acetylneuraminic acid.

One group of new derivatives according to the invention is represented by the following formulae, wherein only one of the $R_3$ substituents signifies acyl.

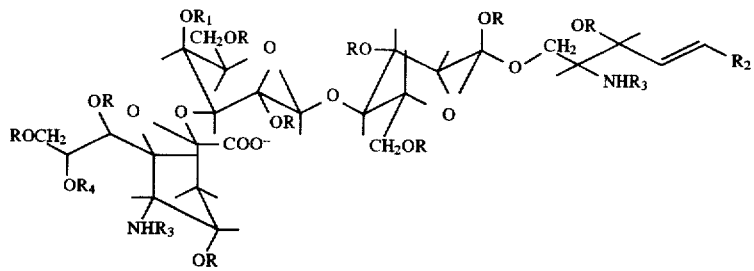

wherein:
R=H or $SO_3H$

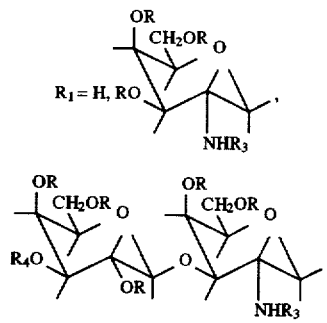

$R_2$=—$(CH_2)_n$—$CH_3$, wherein n=12–14

$R_3$=H, acyl or $SO_2R_5$, provided that at least one is $SO_2R_5$

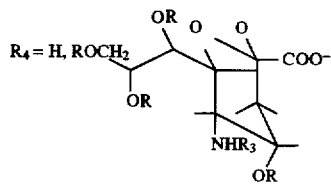

$R_5$=alkyl, aryl or OX
(X=H, alkyl, aryl)

Of the specific compounds of particular interest, special mention should be made of the following derivatives of N-lyso $GM_1$ (ganglioside $GM_1$ without its acyl group in the ceramide residue):

N-ethyl-sulfonyl-lyso-$GM_1$
N-propyl-sulfonyl-lyso-$GM_1$
N-n-butyl-sulfonyl-lyso-$GM_1$
N-n-pentyl-sulfonyl-lyso-$GM_1$
N-n-hexyl-sulfonyl-lyso-$GM_1$
N-n-heptyl-sulfonyl-lyso-$GM_1$
N-n-octyl-sulfonyl-lyso-$GM_1$
N-n-decyl-sulfonyl-lyso-$GM_1$
N-2-bromoethyl-sulfonyl-lyso-$GM_1$
N-hexadecyl-sulfonyl-lyso-$GM_1$
N-3-chloropropyl-sulfonyl-lyso-$GM_1$
N-6-bromohexyl-sulfonyl-lyso-$GM_1$
N-benzyl-sulfonyl-lyso-$GM_1$
N-4-chlorobenzyl-sulfonyl-lyso-$GM_1$
N-4-aminobenzyl-sulfonyl-lyso-$GM_1$
N-3,4,5-trimethoxybenzyl-sulfonyl-lyso-$GM_1$
N-sulfo-lyso-$GM_1$ Moreover, interesting compounds are derivatives sulfated at the hydroxy groups of each of the compounds specifically mentioned, which can be partially sulfated derivatives containing for example just one sulfated group (sulfo) on one of the saccharide hydroxyl groups and which are mixtures of various position isomers, or are persulfated derivatives, wherein all the hydroxyl groups in the ganglioside molecule are converted into esters of sulfuric acid.

Also of interest are the derivatives corresponding to those which appear in the aforementioned list, deriving however from one of the following gangliosides: $GM_4$, $GM_3$, $GM_2$, $GD_2$, $GD_{1a}$, $GT_1$.

Of the derivatives of N'-lyso-$GM_1$ (i.e. ganglioside $GM_1$ without its acyl group in the neuraminic residue), special mention should be made of N'alkyl-sulfonyl-N'-lyso-$GM_1$, the alkyl of which is any one of the alkyl groups appearing in the above list for N-lyso-$GM_1$ derivatives, and N'aryl-sulfonyl-N'-lyso-$GM_1$, the aryl group of which is any one of the specific groups of this type mentioned above and N'-sulfo-N'-lyso-$GM_1$ and the esters thereof with alcohols deriving from any one of the alkyl or aryl radicals featured in said N-alkyl or aryl-sulfonyl-$GM_1$ derivatives, and the derivatives thereof partially or totally sulfated at the hydroxyls groups. Of the derivatives of N,N'-dilyso-$GM_1$ (i.e. ganglioside $GM_1$ from which both acyl groups have been removed from the ceramide and the neuraminic group) mention should be made of the N,N'-di-alky- and N,N'-di-aryl-sulfonyl-N,N'-di-lyso-$GM_1$, with an alkyl or an aryl corresponding to the specific groups of this type which is featured in the above reported list of the N-alkyl- or N-aryl-sulfonyl-lyso-$GM_1$. Mention should also be made of the derivatives wherein one of the amino groups of ganglioside $GM_1$ is acylated with an alkyl or arylsulfonic acid, wherein alkyl or aryl is one of the aforesaid specific groups in the list reported above for the derivatives of N-lyso-$GM_1$ and the other amino group is acylated with an acid selected from the group consisting of acetic acid, chloroacetic acid, dichloroacetic acid, propionic acid, n-valerianic acid, trimethylacetic acid, caproic and hexanoic acid, caprylic acid and undecylic acid, and in particular the di-sulfo derivative of N,N'-di-lyso-$GM_1$, and the esters thereof with alcohols deriving from any one of the alkyl or aryl radicals featuring in the above list of derivatives of N-alkyl- or N-aryl-sulfonyl-lyso-GM1.

Thus, specific compounds are
N'-ethyl-sulfonyl-N'-lyso-$GM_1$
N'-propyl-sulfonyl-N'-lyso-$GM_1$
N'-n-butyl-sulfonyl-N'-lyso-$GM_1$
N'-n-pentyl-sulfonyl-N'-lyso-$GM_1$
N'-n-hexyl-sulfonyl-N'-lyso-$GM_1$
N'-n-heptyl-sulfonyl-N'-lyso-$GM_1$
N'-n-octyl-sulfonyl-N'-lyso-$GM_1$
N'-n-decyl-sulfonyl-N'-lyso-$GM_1$ N'-2-bromoethyl-sulfonyl-N'-lyso-GM$_1$
N'-hexadecyl-sulfonyl-N'-lyso-GM$_1$
N'-3-chloropropyl-sulfonyl-N'-lyso-GM$_1$
N'-6-bromohexyl-sulfonyl-N'-lyso-GM$_1$
N'-benzyl-sulfonyl-N'-lyso-GM$_1$
N'-4-chlorobenzyl-sulfonyl-N'-lyso-GM$_1$
N'-4-aminobenzyl-sulfonyl-N'-lyso-GM$_1$
N'-3,4,5-trimethoxybenzyl-sulfonyl-N'-lyso-GM$_1$
N'-sulfo-N'-lyso-GM$_1$
N,N'-di(ethyl-sulfonyl)-N,N'-dilyso-GM$_1$
N,N'-di(propyl-sulfonyl)-N,N'-dilyso-GM$_1$
N,N'-di-(n-butyl-sulfonyl)-N,N'-dilyso-GM$_1$
N,N'-di-(n-pentyl-sulfonyl)-N,N'-dilyso-GM$_1$
N,N'-di- (n-hexyl-sulfonyl)-N,N'-dilyso-GM$_1$
N,N'-di-(n-heptyl-sulfonyl)-N,N'-dilyso-GM$_1$
N,N'-di-(n-octyl-sulfonyl)-N,N'-dilyso-GM$_1$
N,N'-di-(n-decyl-sulfonyl)-N,N'-dilyso-GM$_1$
N,N'-di-(2-bromoethyl-sulfonyl)-N,N'-dilyso-GM$_1$
N,N'-di-hexadecyl-sulfonyl-N,N'-dilyso-GM$_1$
N,N'-di-(3-chloropropyl-sulfonyl)-N,N'-dilyso-GM$_1$
N,N'-di-(6-bromohexyl-sulfonyl)-N,N'-dilyso-GM$_1$
N,N'-di-benzyl-sulfonyl-N,N'-dilyso-GM$_1$
N,N'-di-(4-chlorobenzyl-sulfonyl)-N,N'-dilyso-GM$_1$
N,N'-di-(4-aminobenzyl-sulfonyl)-N,N'-dilyso-GM$_1$
N,N'-di-(3,4,5-trimethoxybenzyl-sulfonyl)-N,N'-dilyso-GM$_1$
N,N'-di-sulfo-N,N'-(dilyso-GM$_1$
N-ethyl-sulfonyl-N'-acyl-N,N'-dilyso-GM$_1$
N-propyl-sulfonyl-N'-acyl-N,N'-dilyso-GM$_1$
N-n-butyl-sulfonyl-N'-acyl-N,N'-dilyso-GM$_1$
N-n-pentyl-sulfonyl-N'-acyl-N,N'-dilyso-GM$_1$
N-n-hexyl-sulfonyl-N'-acyl-N,N'-dilyso-GM$_1$
N-n-heptyl-sulfonyl-N'-acyl-N,N'-dilyso-GM$_1$
N-n-octyl-sulfonyl-N'-acyl-N,N'-dilyso-GM$_1$
N-n-decyl-sulfonyl-N'-acyl-N,N'-dilyso-GM$_1$
N-2-bromoethyl-sulfonyl-N'-acyl-N,N'-dilyso-GM$_1$
N-hexadecyl-sulfonyl-N'-acyl-N,N'-dilyso-GM$_1$
N-3-chloropropyl-sulfonyl-N'-acyl-N,N'-dilyso-GM$_1$
N-6-bromohexyl-sulfonyl-N'-acyl-N,N'-dilyso-GM$_1$
N-benzyl-sulfonyl-N'-acyl-N,N'-dilyso-GM$_1$
N-4-chlorobenzyl-sulfonyl-N'-acyl-N,N'-dilyso-GM$_1$
N-4-aminobenzyl-sulfonyl-N'-acyl-N,N'-dilyso-GM$_1$
N-3,4,5-trimethoxybenzyl-sulfonyl-N'-acyl-N,N'-dilyso-GM$_1$
N-sulfo-N'-acyl-N,N'-dilyso-GM$_1$
and
N-acyl-N'-ethylsulfonyl-N,N'-dilyso-GM$_1$
N-acyl-N'-propyl-sulfonyl-N,N'-dilyso-GM$_1$
N-acyl-N'-n-butyl-sulfonyl-N,N'-dilyso-GM$_1$
N-acyl-N'-n-pentyl-sulfonyl-N,N'-dilyso-GM$_1$
N-acyl-N'-n-hexyl-sulfonyl-N,N'-dilyso-GM$_1$
N-acyl-N'-n-heptyl-sulfonyl-N,N'-dilyso-GM$_1$
N-acyl-N'-n-octyl-sulfonyl-N,N'-dilyso-GM$_1$
N-acyl-N'-n-decyl-sulfonyl-N,N'-dilyso-GM$_1$
N-acyl-N'-2-bromoethyl-sulfonyl-N,N'-dilyso-GM$_1$
N-acyl-N'-hexadecyl-sulfonyl-N,N'-dilyso-GM$_1$
N-acyl-N'-3-chloropropyl-sulfonyl-N,N'-dilyso-GM$_1$
N-acyl-N'-6-bromohexyl-sulfonyl-N,N'-dilyso-GM$_1$
N-acyl-N'-benzyl-sulfonyl-N,N'-dilyso-GM$_1$
N-acyl-N'-4-chlorobenzyl-sulfonyl-N,N'-dilyso-GM$_1$
N-acyl-N'-4-aminobenzyl-sulfonyl-N,N'-dilyso-GM$_1$
N-acyl-N'-3,4,5-trimethoxybenzyl-sulfonyl-N,N'-dilyso-GM$_1$
N-acyl-N'-sulfo-N,N'-dilyso-GM$_1$
wherein "acyl" designates the acyl radical of acetic acid, chloroacetic acid, dichloroacetic acid, propionic acid, n-valerianic acid, trimethylacetic acid, caproic and hexanoic acid, caprylic acid and undecylic acid and the esters thereof with alcohols selected from the group consisting of ethyl alcohol, propyl alcohol, n-butyl alcohol, n-pentyl alcohol, n-hexyl alcohol, n-heptyl alcohol, n-octyl alcohol, n-decyl alcohol, 2-bromoethyl alcohol, hexadecyl alcohol, 3-chloropropylalcohol, 6-bromohexylalcohol, benzyl alcohol, 4-chlorobenzyl alcohol, 4-aminobenzyl alcohol and 3,4,5-trimethoxybenzyl alcohol.

With these derivatives it is also possible to prepare the corresponding esters of sulfuric acid at the hydroxyl groups, i.e. partially or totally sulfated derivatives.

THERAPEUTIC ACTIVITY

It is well known that gangliosides are glycosphingolipids containing sialic acid with a basic saccharide structure bound to ceramide and one or more molecules of sialic acid. The saccharide portion presents at least one galactose or glucose unit and one N-acetylglucosamine or N-acetylgalactosamine.

The general structure of a ganglioside can so be represented as follows:

| One | - One mole of ceramide |
| mole | - At least one mole of galactose |
| of | or glucose |
| sialic | - At least one mole of N-acetylglucosamine |
| acid | or N-acetylgalactosamine | where all the components are bound by glucosidic bonds.

A large number of gangliosides have been identified which are particularly abundant in the nervous tissue, especially in the cerebral one (Ando S.: Gangliosides in the nervous system. Neurochem. Int. 5, 507537, 1983).

It has been widely demonstrated that gangliosides are able to enhance functional recovery both in the lesioned Periferal Nervous System (PNS) and Central Nervous System (CNS), through the involvement of specific membrane mechanisms and the interaction with trophic factors, as pointed out from studies in vitro on neuronal cultures (Ferrari F. et al.: Dev. Brain Res., 8:215–221, 1983; Doherty P. et al., J. Neurochem. 44: 1259–1265, 1985; Skaper S. D. et al., Mol. Neurobiol. 3:173–199, 1989).

Moreover, it has been shown that gangliosides are able to selectively act where mechanisms responsible for neurotoxicity have been activated, thus antagonizing the effects of the paroxysmal and continuous stimulation of the excitatory amino acid receptors (Favaron M. et al.: Gangliosides prevent glutamate and kainate neurotoxicity in primary neuronal cultures of neonatal rat cerebellum and cortex. Proc. Natl. Acad. Sci. 85: 7351–7355, 1988).

Concerning the PNS, the effects of the ganglioside mixture have been reported in models of traumatic (Gorio A. et al., Brain Res. 197: 236241, 1980), metabolic (Norido F. et al., Exp. Neurol. 83: 221–232, 1984) and toxic (Di Gregorio F. et al., Cancer Chemother. Pharmacol. 26: 3136, 1990) neuropathies. Concerning the CNS, the positive effects of recovery induced by the monosialoganglioside GM$_1$ have been widely described in ischemia models (Karpiak S. E. et al., CRC Critical Rev. in Neurobiology. vol. 5. Issue 3, pp. 221–237, 1990), as well as in traumatic (Toffano G. et al., Brain Res. 296: 233–239, 1984) and neurotoxic (Schneider et al., Science 256: 843–846, 1992) lesions. Such results have led to the clinical application of GM$_1$ in conditions of ischemic brain injury (Argentino C. et al., Stroke 20: 1143–1149, 1989) and in conditions of traumatic injury of the spinal cord (Geisler F. H., N. Engl. J. Med. 324: 1829–1838, 1991).

In addition, it has been recently shown that gangliosides are involved in the modulation of the expression of the receptors named $CD_4$, which are present on the membrane of some lymphocytes and furthermore it has been shown that such a modulation is associated with an inhibition of the proliferation of the HIV virus (Offner H. et al.: Gangliosides induce selective modulation of $CD_4$ from helper T lymphocytes. J. Immunol. 139: 3295–3305, 1987; Grassi F. et al.: Chemical residues of ganglioside molecules involved in interactions with lymphocyte surface targets leading to $CD_4$ masking and inhibition of mitogenic proliferation. Eur. J. Immunol. 20: 145–150, 1990; Chieco-Bianchi et al. $CD_4$ modulation and inhibition of HIV-1 infectivity induced by monosialoganglioside $GM_1$ in vitro. AIDS 3:501–507, 1989).

The molecule named $CD_4$ is a membrane glycoprotein of 55 KDa expressed by thymocytes, by a "subset" of T lymphocytes and, at a lower density, by monocytes/macrophages. The molecule can be divided into three portions: one extracellular, that is divided into 4 domains, three of which have a structure that joins them to the superfamily of immunoglobulins, an intra-membrane portion of 21 amino acids (aa), and an intracytosolic portion of 40 basic aa.

In T lymphocytes $CD_4$ has at least two functions. On one hand, it interacts with a non-polymorphic region of class II HLA molecules, thus stabilizing the bond between the T cell and the cell which expresses the antigen (secondary role). On the other hand, recent evidence have shown how the interaction of $CD_4$ with its own ligand induces the activation of a cytoplasmic tyrosine kinase (named p56 lck) that is in contact with the intracytosolic portion of $CD_4$. The activation of the tyrosine kinase and the subsequent phosphorylation of different substrates, among them the gamma chain of $CD_3$, has a facilitatory role in the signal transduction following the interaction between the antigen receptor and the antigen itself. Hence, $CD_4$ has an active role in the mechanisms that regulate the activation of T lymphocytes.

In addition to these relevant functions for the physiology of T cells, $CD_4$ is also the receptor utilized by HIV viruses to enter the target cells.

The $CD_{4+}$ T lymphocytes play a major role in immune system functioning. In the majority of cases, following contact with the antigen the first cells responsible for any adaptative response are the $CD_{4+}$ T cells, which after the activation, may become in turn effectors of response. Alternatively, the activated $CD_{4+}$ cells can help, by release of cytokines, other cells (B cells, $CD_{8+}$ T cells) to become effectors of response. This is valid both for responses against foreign antigens (non-self) and for body antigens (self). Thus, $CD_{4+}$ T cells are primarily involved in several autoimmune diseases.

The possibility of modulating the $CD_{4+}$ T cell function is relevant in a wide range of human pathologies.

In different models, both in vitro and in vivo, it has been shown that by blocking the $CD_4$ molecule with monoclonal antibodies, the function of $CD_{4+}$ T cells is inhibited. Such an inhibition leads in turn to unsuccessful proliferation, unsuccessful production of cytokines, unsuccessful production of antibodies, and suppression or lowering of clinical expression of autoimmune symptoms in experimental models of autoimmune pathology.

The pharmacological properties of the new sulfated derivatives, according to the present invention, can be emphasized by the experimental studies performed on the following compounds:

N-4-CHLOROBENZENESULFONYL-LYSO $GM_1$ (Liga 123)

N-BENZENESULFONYL-LYSO $GM_1$ (Liga 125)

N'-O-SULFO-LYSO $GM_1$ (Liga 179)

Hereinafter will be described the experimental models and the results obtained with some representative compounds of the present invention.

1. Antineurotoxic effect of Liga 123 in vitro in cerebellar granule cells: protective effect against neurotoxicity induced by exogenous glutamate.

MATERIALS AND METHODS

Cell cultures

Primary cultures of cerebellar granule cells have been prepared from 8-day-old Sprague-Dawley rats.

Neurons have been grown in 35 mm dishes for 11–13 days and kept in a humidified environment (95% air and 5% CO2) at 37° C. Cultures ($2.5 \times 10^6$ cells/dish) were mainly constituted of granular cells (>95%) with a low percentage (<5%) of glial cells (Gallo V. et al.: Selective release of glutamate from cerebellar granule cells differentiating in culture. Proc. Natl. Acad. Sci. USA 79, 7919–7923, 1982). Glial proliferation was prevented by cytosine arabinofuranoside.

The Liga 123 derivative has been solubilized in chloroform/methanol (2/1), then dried under a nitrogen flow and diluted at different concentrations in Locke's solution (154 mM NaCl, 5.6 mM KCl, 3.6 mM $NaHCO_3$, 2.3 mM $CaCl_2$, 1 mM $MgCl_2$, 5.6 mM glucose, 4.6 mM Hepes, pH 7.4).

Concentrations from 100 µM to 5 µM have been tested. Description of the model of neurotoxicity induced by exogenous glutamate.: compound in a pretreatment paradigm.

The cell culture medium was aspirated from the dishes (and properly stored). The dishes were washed (3×2 ml) with Locke's solution, then the solutions (1.5 ml) containing the compound to be tested were added, and incubated for 2 hrs in incubator at 37° C. (5% $CO_2$).

The treated cells were washed (3×2 ml) with Locke's solution+10% fetal calf serum heat inactivated (without glutamic acid), then washed (3×2 ml) in Locke's solution in the absence of $Mg^{2+}$. Glutamate was added at 100 µM (1.5 ml) in Locke's solution ($-Mg^{2+}$) or Locke's solution alone ($Mg^{2+}$) was added (controls). The incubation with glutamate or with Locke's ($-Mg^{2+}$) was performed for 60 minutes at room temperature (27° C.). The glutamate was then removed, the dishes were washed with Locke's solution ($+Mg^{2+}$) (2×2 ml), then incubated in the presence of the initial medium (properly stored) for 24 hr at 37° C. in incubator (5% $CO_2$).

At the end of the incubation the cell viability measured by using the MTT colorimetric test was evaluated (Mosmann T., Rapid colorimetric assay for cellular growth and survival: application to proliferation and cytotoxicity assays. J. Immunol. Meth. 65, 55–63, 1983 and modified according to Skaper S. D. et al.: Death of cultured hippocampal pyramidal neurons induced by pathological activation of N-methyl-Daspartate receptors is reduced by monosialogangliosides. J. Pharm. and Exp. Ther. 259, 1, 452–457, 1991). The data are expressed as $ED_{50}$ (µM).

RESULTS

The obtained results (Table 1) show that the Liga 123 compound has a marked antineurotoxic activity ($ED_{50}=6$ µM): the neuroprotective effect of Liga 123, at a concentration of 25 µM, is about 74%.

TABLE 1

Antineuronotoxic effect of Liga 123 in cerebellar granule cells: protective effect on neurotoxicity induced by exogenous glutamate

| Groups | (concentrations µM) | % survival (±SD) |
|---|---|---|
| 1) control | | 100 |
| 2) glutamate | | 19 ± 1 |
| 3) glutamate + Liga 123 | 25 µM | 74 ± 5 |
| | 10 µM | 63 ± 6 |
| | 5 µM | 35 ± 3 |

2. Antineurotoxic effect of Liga 179 in vitro in cerebellar granule cells: compound in cotreatment paradigm with glutamic acid

MATERIALS AND METHODS

Cell cultures

Primary cultures of cerebellar granule cells have been prepared according to the method described in Materials and Methods of the preceding experiment (1).

The Liga 179 derivative has been dissolved in sterile water at a concentration of 50 mM. Thus, dilutions have been performed at different concentrations in Locke's solution (154 mM NaCl, 5.6 mM KCl, 3.6 mM NaHCO$_3$, 2.3 mM CaCl$_2$, 5.6 mM glucose, 4.6 mM Hepes, pH 7.4).

Concentrations from 100 µM to 5 µM have been tested.

Compound in cotreatment paradigm with glutamic acid

The cell culture medium was aspirated from the dishes (and properly stored). The dishes were washed (3×2 ml) with Locke's solution in the absence of Mg$^{2+}$. Then, 1.5 ml of Locke's solution (−Mg$^{2+}$) with or without 100 µM glutamate and with or without the compound to be tested were added. The incubation period lasted 30 minutes (37° C.). Glutamate and the compound to be tested were then removed. The dishes were washed with Locke's solution in the presence of Mg$^{2+}$ (2×2 ml) and then incubated in the presence of the initial medium (properly stored) for 24 hours at 37° C. in an incubator (5% CO$_2$).

At the end of the incubation cell viability measured by means of the MTT colorimetric test was evaluated (Mosmann T.: Rapid colorimetric assay for cellular growth and survival: application to proliferation and cytotoxicity assays. J Immunol. Meth. 65, 55–63, 1983 and modified according to Skaper S. D. et al.: Death of cultured hippocampal pyramidal neurons induced by pathological activation of N-methyl-D-aspartate receptors is reduced by monosialogangliosides. J. Pharm. and Exp. Ther. 259,1, 452–457, 1991). Data were expressed as ED$_{50}$ (µM).

RESULTS

The data obtained (Table 2) show that the Liga 179 compound has a marked antineurotoxic activity (ED$_{50}$=15 µM), even when administered simultaneously with glutamate (co-treatment): the neuroprotective effect of Liga 179 is clear already at 10 µM and reaches its maximum effect at 50 µM.

TABLE 2

Antineurotoxic effect of Liga 179 in simultaneous treatment with exogenous glutamate in cerebellar granule cells (protective effect).

| Groups | (Concentration µM) | % survival (average ± s.d.) |
|---|---|---|
| 1) control (−Mg2+) | | 100 |
| 2) glutamate | | 33 ± 1 |
| 3) glutamate + Liga 179 | 100 µM | 125 ± 5 |
| | 50 µM | 133 ± 9 |
| | 10 µM | 52 ± 4 |

3. Neuritogenic activity of the compounds Liga 123 and Liga 125

MATERIALS AND METHODS

Cell Cultures

Mouse neuroblastoma cells C1300, Neuro-2A clone (obtained from American Cell Type Culture Collection—Bethesda, Md.) have been seeded at a density of 10,000 cells/well (24-Falcon) in tissue culture medium containing Dulbecco's modified Eagle medium (DMEM, Gibco), 10% fetal calf serum heat inactivated (FCS, lot 7201 Seromed), penicillin (100 units per ml, Irvine) and L-glutamine (2 mM, Sigma). Cells have been incubated at 37° C. for 24 hr, then the medium was withdrawn and substituted with 350 µl of fresh culture medium with and without the compounds to be tested.

Compounds under examination and their solubilization

The derivatives have been solubilized in chloroform/methanol (2/1) and then dried under a flow of nitrogen.

For the different compounds, consecutive dilutions in tissue culture medium (concentrations from 50 µM to 5 µM) were performed.

Parameters: neuritogenic activity (% of neurite-bearing cells under the optical microscope).

Culture dishes incubated with the tested compounds were analyzed under a phase contrast microscope (250×): 9 optical fields were chosen with prefixed coordinates and photographed. Then, the total number of cells were counted, as well as the number of neurite-bearing cells (length at least double of the cell diameter) in blind on every picture. The percentage of neurite-bearing cells was determined following the counting of at least 100 cells, and the data were expressed by the respective ED$_{50}$ (µM) (Facci L. et al.: Promotion of neuritogenesis in mouse neuroblastoma cells by exogenous ganglioside GM$_1$. J. Neurochem. 229–305, 1984).

RESULTS

The results obtained (Table 3) show that the Liga 123 and 125 derivatives promote neuritogenesis in vitro. In particular, in the experimental conditions tested, it turns out that:

the neuritogenic effect is remarkable for the Liga 123 derivative: at a dose of 25 µM, about 48% of the cells present long and ramified neurites.

the neuritogenic effect with Liga 126 is maximal at a dose of 50 µM (56% of neurite-bearing cells).

TABLE 3

Neuritogenic effect of Liga 123 and 125 in neuroblastoma cells N2A

| Compounds | ED$_{50}$ (µM) |
|---|---|
| Liga 123 | 12 µM |
| Liga 125 | 25 µM |

4. Effect of Liga 179 on the expression of the CD$_4$ molecule in Molt 3 cells

Molt 3 cells (American Type Culture Collection— Rockville, Md., USA) have been utilized, human tumoral cell lines derived from an acute lymphoblastic leukemia and formed by T lymphocytes expressing CD$_4$ on their surface. Such a cell line was chosen due to the fact that it overlaps, as regards the expression of the CD$_4$ molecule, human T lymphocytes obtained from peripheral blood. 100% of Molt 3 cells express CD$_4$, whereas only part of human T lymphocytes from peripheral blood express CD$_4$ in a proportion varying from subject to subject. The Molt 3 model has therefore the advantage of allowing a better experimental reliability.

MATERIALS AND METHODS

Molt 3 cells (1×10$^6$) have been incubated with different concentrations of Liga 179 (from 1 µg/ml to 500 µg/ml) for 60 minutes at 37° C. in buffered saline (PBS), with or without Fetal Calf Serum (FCS). When utilized, FCS was added at a concentration of 5 or 10 part/percentage (vol/vol). Following the incubation and the subsequent washing the percentage of cells expressing CD$_4$ has been measured by flow cytofluorimetry using a monoclonal, fluoresceinated (mAb), specific for CD$_4$ (DAKO T4, Dakopatts, Glostrup, Denmark) and a cytofluorimeter (EPICS V, Coulter Electronics, Hialeah, Fla., USA).

In Table 4 are reported the data concerning the percentage of Molt 3 cells that express CD$_4$, following the incubation with the compound under examination at the different concentrations utilized.

TABLE 4

Effect of Liga 179 on the expression of CD4 in Molt 3 cells
% MOLT-3 cells expressing CD$_4$ on the surface

| Compound | µg/ml | FCS (%) 0 | FCS (%) 5 | FCS (%) 10 |
|---|---|---|---|---|
| Liga 179 | 0 | 96.9 | 98.6 | 96.9 |
| Liga 179 | 10 | 0 | — | — |
| Liga 179 | 50 | 0 | — | — |
| Liga 179 | 100 | 0 | 15.5 | 86.5 |
| Liga 179 | 200 | — | 0 | 14.6 |
| Liga 179 | 500 | — | 0 | 0 |

The results reported in Table 4 show how the modulating effect of Liga 179 can be expressed in a dose/response curve, and how increasing doses of serum require increasing concentrations of Liga 179.

It is important to point out that, at the highest concentration of serum, the Liga 179 compound is able to totally inhibit the expression of CD$_4$.

CONCLUSIONS

The above-described results show a remarkably interesting pharmacological profile of the new compounds, which are object of the present invention. Special mention should be made of the antineurotoxic effect on CNS cells, and the modulatory effect on the expression of the CD$_4$ molecule in the immune system cells.

In consideration of the antineurotoxic effect, the novel derivatives of the neuraminic acid may be successfully used in disorders associated with an excitatory activity of the excitatory amino acids. It has been demonstrated that such amino acids, e.g., the glutamic or aspartic acid, besides their major role in different physiological processes, e.g. synaptogenesis and neuronal plasticity, are involved in the etiogenesis and/or evolution of different disorders with neuronal dysfunctions and/or death. Even though neuronal damage may have different causes, the neuronal dysfunctions trigger a cascade of cellular events, such as the activation of enzymatic reactions depending on Ca$^{+2}$ ions, the influence of Ca$^{+2}$ ions, the activation of secondary messengers, which result in neuronal death. Hence, a further aspect of the invention is directed to a method for treating conditions related to neurotoxicity induced by excitatory amino acids which comprises administration of a compound according to the invention, together with a pharmaceutically acceptable excipient, to a patient in need therefor. Damage to the CNS caused by excitatory amino acids appears for instance in ischemia, epilepsy, trauma, compression, metabolic dysfunctions, aging, toxic-infective disorders, as well as in chronic neurodegenerative disorders, such as Alzheimer's disease or Huntington's chorea (Engelsen B., Acta Neurol. Scand. "Neurotransmitter glutamate: its clinical importance", 186, 4, 337355; Olney J. W., Annu. Rev. Pharmacol. Toxicol., "Exctatotoxic amino acids and neuropsychiatric disorders", 1990, 30, 47–71).

In addition, the novel compounds which are object of the present invention, in consideration of their neurite-promoting activity, may be used with advantage in the treatments aiming at nerve function recovery in those pathological conditions associated with a neuronal damage, such as peripheral neuropathies.

Moreover, the capacity of such compounds to modulate the expression of the CD$_4$ molecule on immune cell surface, may be of great relevance in a wide range of human pathologies, e.g., those situations in which it is necessary to prevent and/or treat infections in which CD$_4$ cells are involved (especially infections whose etiological agents are microorganisms belonging to the HIV virus family). Moreover, modulation of CD$_4$ is useful in systemic or organ-specific autoimmune diseases, such as multiple sclerosis, rheumatoid arthritis, chronic polyarthritis, lupus erythematosus, juvenile-onset diabetes mellitus and also to prevent the phenomenon of organ transplant rejection as well as rejection by the transplanted material against the host, as in the case of bone marrow transplant, and in all cases where the desired effect is to obtain tolerance towards "self" and "non-self" antigens.

The present invention includes also processes for the preparation of new compounds. Such processes involve conventional and well-documented approaches for the conversion of an amino group into its acylated derivative or for the selective hydrolysis of acyl derivatives of amino groups, and optionally for the esterification of functional groups, specifically, the carboxyl groups, or for the esterification of hydroxyl groups. Thus, the process for the preparation of new compounds consists in treating a N,N'-di-lyso-ganglioside or one of its N- or N'-acyl derivatives with sulfuric acid, a hydrocarboxyl-sulfuric acid or a hydrocarbylsulfonic acid or their reactive derivative, if desired, acylating an amino group in position N- or N'- and, if desired, hydrolyzing in the obtained compounds one of the two acylated amino groups thereby converting them into free amino groups and optionally converting free carboxyl groups or free hydroxyl groups into their functional derivatives and optionally converting the obtained compounds into their metal salts or salts deriving from organic bases, or into their acid addition salts.

The process also involves those modifications in which the procedure is interrupted at any phase and, if desired, the remaining steps are performed or in which the procedure is started from an intermediate and the remaining steps are performed or in which an "in situ" intermediate is formed.

The lyso-gangliosides may be prepared from gangliosides or from N-lyso-gangliosides by alkaline hydrolysis, for example with tetraalkylammonium hydroxides, sodium hydroxide or similar agents.

The preparation of N- or N'-mono or poly-acyl-derivatives from N,N'-dilyso-gangliosides is described in literature.

Compounds having an acyl group on the neuraminic nitrogen can be prepared by various methods. It is possible, for example, to start with dilyso-gangliosides and then effect an intermediate provisional protection of the sphingosine amino group, which can be done for example by hydrophobic interaction with phosphatidylcholine, or by acylation with suitable protective groups, subsequent acylation on the neuraminic nitrogen with a derivative of the acid which is to be introduced into this position, and then deprotection on the sphingosine nitrogen. Alternatively, dilyso-gangliosides can be acylated on the two amino groups with the same acid and the diacyl compound can be exposed to the action of enzymes which are able to selectively remove the acylamino groups from the sphingosine nitrogen, for example enzymes used to obtain lyso-gangliosides from gangliosides, such as the glycosphingolipid-ceramide-deacylase enzyme (see scheme 1). N-monoacyl-N,N'-dilyso-gangliosides can however also be obtained by deacylating N,N'-diacyl-N,N'-dilyso-gangliosides on the neuraminic nitrogen by selective chemical hydrolysis, for example with 0.1 molar alcoholic potassium hydroxide.

The procedure for the preparation of N-acyl-N,N'-dilyso-gangliosides comprises acylating N,N'-di-lyso-gangliosides with the acids corresponding to the acyl group to be introduced or selectively deacylating suitable N,N'-diacyl-N,N'-dilyso-gangliosides on the neuraminic nitrogen.

N-acylation according to the aforesaid procedure can be effected in the conventional manner, for example by reacting the starting products with an acylating agent, especially with a functional derivative of the acid, the residue of which is to be introduced. Thus, it is possible to use a halide or an anhydride as the functional derivative of the acid, and the acylation is carried out preferably in the presence of a tertiary base, such as pyridine or collidine. Anhydrous conditions can be used at room temperature or at higher temperatures, or the Schotten-Baumann method can also be used to advantage, operating in aqueous conditions in the presence of an organic base. In some cases it is also possible to use esters of the acids as reactive functional derivatives. Of all the preparation methods, the following are the most appropriate:

1. reaction of the lyso-ganglioside derivative with the azide of the acid;
2. reaction of the lyso-ganglioside derivative with an acylimidazole of the acid obtainable from the acid with N,N'-carbonyldiimidazole;
3. reaction of the lyso-ganglioside derivative with a mixed anhydride of the acid and of trifluoroacetic acid;
4. reaction of the lyso-ganglioside derivative with the chloride of the acid;
5. reaction of the lyso-ganglioside derivative with the acid in the presence of a carbodiimid (such as dicyclohexylcarbodiimide) and optionally a substance such as 1-hydroxybenzotriazole;
6. reaction of the lyso-ganglioside derivative with the acid by heating;
7. reaction of the lyso-ganglioside derivative with a methyl ester of the acid at a high temperature;
8. reaction of the lyso-ganglioside derivative with a phenol ester of the acid, for example an ester with para-nitrophenol;
9. reaction of the lyso-ganglioside derivative with an ester derived from the exchange between a salt of the acid and 1-methyl-2-chloropyridinium iodide.

It has already been explained how it is possible to obtain selective partial acylation both on the sphingosine and on the neuraminic nitrogen. Scheme 1 illustrates these procedures.

Enzymatic deacylation of N,N'-diacyl-N,N'- dilyso-gangliosides on the sphingosine nitrogen as previously reported can be effected under the same conditions as those used for the partial deacylation of gangliosides, for example as described in J. Biochem., 103, 1 (1988). The double deacylation of N,N'-diacyl-N,N'-dilyso-gangliosides to N,N'-dilyso-gangliosides can be effected in the same way as the preparation of de-N-acetyl-lyso-gangliosides as described for example in Biochemistry 24, 525 (1985); J. Biol. Chem. 255, 7657, (1980); Biol. Chem. Hoppe Seyler 367, 241, (1986): Carbohydr. Research 179, 393 (1988); Bioch. Bioph. Res. Comn. 147, 127 (1987).

The aforesaid publication in Carbohydr. Research 179 also describes a method for selective deacylation on the neuraminic nitrogen by the action of KOH (0.1M) in 90% normal butanol with the ganglioside $GM_3$. This type of deacylation reaction can be applied to N,N'-diacyl-N,N'-dilyso-gangliosides to obtain N-acyl-N,N'-dilyso-gangliosides.

Scheme 1

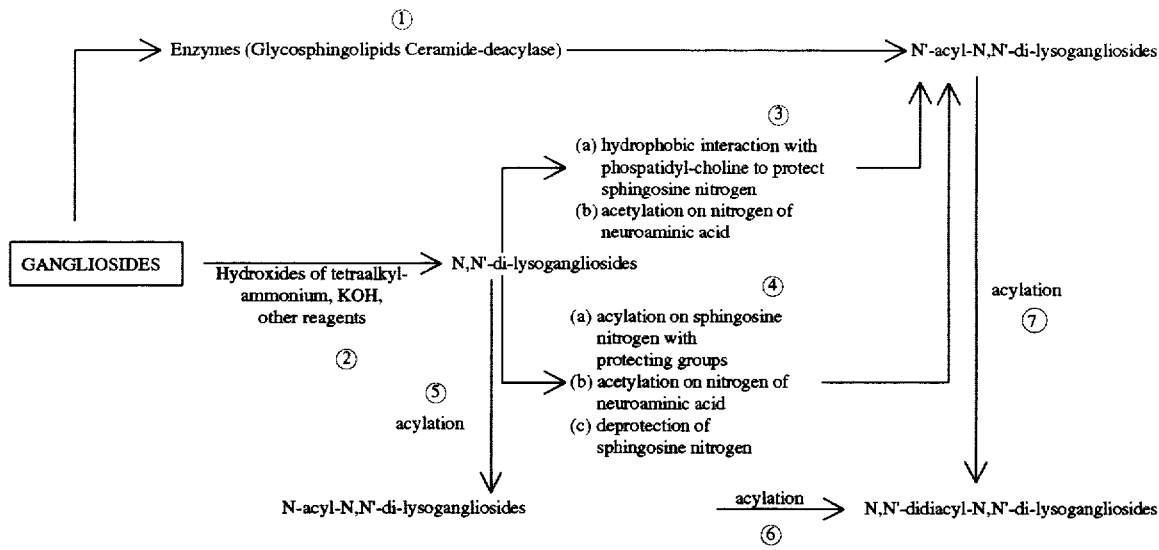

The conversion of N,N'-dilyso-gangliosides into the aforesaid di- and polyderivatives of sulfuric acid, of its esters or of hydrocarbylsulfonic acids may be performed partially, the sphingosine amino group being more reactive than the neuraminic amino group. It is therefore possible to obtain the N-derivatives with the amino group converted with the corresponding acid, and it is also possible, if one wishes, to convert in the same manner the neuraminic amino group in a second step.

The insertion of the sulfo ($SO_2OH$) group into an amino group of the aforesaid N,N'-dilyso-gangliosides (or in both, in all the amino groups respectively) is preferably done with the reactive derivative of the sulfuric acid and its trioxide, respectively; normally, the sulfur trioxide-pyridine complex is used, provided an adequate solvent, for example water, at room temperature.

The insertion of a hydrocarbyl-sulfonyl group is preferably done with a halide such as chloride of the hydrocarbon-sulfonic acid, for example with the chloride or bromide of methanesulfonic or p-toluene-sulfonic acid, in the presence of a tertiary base, such as pyridine, collidine, triethylamine, etc.

The insertion of a hydrocarbyloxy-sulfonyl group occurs by reaction with the corresponding ether of the chlorosulfonic acid, also in the presence of a tertiary base, such as one of the above-mentioned ones.

The optional acylation of the amino groups in position N- or N'- in the compounds containing only one of the said sulfured groups is preferably done with an acylating agent, preferably with a reactive functional derivative of the acid from which the acyl group is to be inserted. Therefore it is possible to use a halide or an anhydride as a functional derivative, and the acylation is preferably done in the presence of a tertiary base, such as pyridine or collidine. It is also possible to work in an anhydrous environment, at room temperature or heating; or even successfully following the method of Schotten-Baumann in an aqueous environment, in the presence of an inorganic base.

For the acylation it is also possible to use methods involving activated carboxyl derivatives, such as the ones used in the chemistry of peptides, for example the method of the mixed anhydrides or derivatives obtainable with carbo-diimide derivatives or the isoxazole salts.

The functional modification to be eventually performed, if desired, on the compounds obtained from the conversion with the said derivatives of sulfured acids or with organic acids is also done according to the well-known methods, hence excluding those methods which could affect the basic ganglioside structure, such as those involving highly acidic agents, or which anyway would be performed in critical alkaline or acidic conditions, or also those methods that would bring forth an unwanted alkylation of the hydroxyl groups of the saccharide, sialic or ceramide portion.

The esterification of the sialic carboxyl groups or their conversion into amides can be performed for example as described in the U.S. Pat. No. 4,713,374 of Dec. 12, 1987.

Amides can be prepared for example according to the following methods:

a) reaction of the carboxyl esters with ammonia or with amines;

b) reaction of derivatives according to the invention with carboxyl groups activated with ammonia or with the amines.

Acylation of the hydroxyl groups on the saccharide, sialic and ceramide portion can be performed, for example by means of an acyl halide or an acid anhydride, preferably in the presence of a tertiary base.

The conversion of the hydroxyl groups into the esters of sulfuric acid, which is to be emphasized in the present invention, can be performed in a well-known manner, for example and, preferably, with the sulfur trioxide/dimethylformamide complex in the presence of a base, such as triethylamine, or with the sulfur trioxide/trimethylamine in dimethylformamide complex, then with trifluoroacetic acid in dichloromethane. (compare: Biochemical and Biophysical Research Communications, Vol. 175, No. 1, Feb. 28, 1991).

With such methods, which can vary according to temperature conditions, solvents used and duration of the reaction, it is possible to obtain partial sulfuric esters of the hydroxyl groups or total esters, hence persulfated compounds.

Referred to the present invention are also pharmaceutical preparations including, as active ingredients, one or more of the novel compounds and, in particular, those above emphasized. Such preparations can be assigned to the oral, rectal, parenteral, local or transdermic administration, thus being in a solid or semisolid form, for example pills, tablets, gelatine capsules, capsules, suppositories, soft gelatine capsules. For parenteral use, predetermined forms for intramuscular or transdermic administration, or forms suitable for infusions or intravenous injection are considered, and they can be therefore prepared as solutions of the active ingredients, or as lyophilized forms of the active ingredients to be mixed before use with one or more excipients or pharmaceutically acceptable solvents, suitable to these uses and osmolarity-compatible with the physiological fluids.

For local administration preparations in the form of sprays, for example nasal sprays, creams and ointments for topical use or bandage adequately prepared for transdermic administration are considered.

The pharmaceutical preparations of the present invention can be administered both to humans and animals in need therefor. They contain preferably 0.01% to 0.1% of the active ingredient in the case of solutions, sprays, ointments and creams, and 1% to 100%—preferably 5% to 50%—of the active ingredient for in the case of solid preparations. Dosage depends oil tile indication, the desired effect, and preferred route of administration, as well as the weight and condition of the patient treated.

The present invention also concerns the therapeutic use of the new semisynthetic analogues for the above-said indications. The daily dose to be administered in human by parenteral route (subcutaneous or intramuscular), or by transdermic or oral route, is generally between 0.5 and 5 mg of the active ingredient per kg of body weight. In the preparations reported hereinafter a dose of 150 mg per unit can be reached.

The following examples illustrate the preparation of the new semisynthetic analogues which are object of the present invention, as well as the preparations that contain them as active ingredients.

EXAMPLE 1

N-SULFO-LYSO $GM_1$ 500 mg (0.39 mM) of N-deacyl-lyso $GM_1$ (N-lyso $GM_1$) are dissolved in 50 ml of $Na_2CO_3$ 0.2M in water. 248.3 ml (1.56 mM) of a sulfur trioxide-pyridine complex are then added; the reaction lasts 15 min at room temperature.

Once the reaction is achieved, dialyze in water, concentrate to 100 mg/ml and precipitate in 10 volumes acetone.

Obtained compound: 470 mg (87% theoretical). The name of the compound is also N-sulfo-N'-acetyl-N,N'-dilyso $GM_1$.

Chromatographed on silica gel plate with chloroform/methanol/$CaCl_2$ 0.3% 60/35/8, it proves to be a unitary compound with Rf=0.14 ($GM_1$=0.40, N-deacyl-lyso $GM_1$= 0.17).

EXAMPLE 2

N-SULFO-LYSO $GM_2$ 100 mg (0.071 mM) of $GM_2$ are dissolved in 2 ml KOH 3M and reaction lasts 60 hours at 90° C. Once the reaction is achieved, cool the solution and bring it to pH 6.5 with hydrochloric acid. Keep for 18 hours at 4° C., then filtrate the separated fatty acids. Dialyze against $H_2O$, concentrate and precipitate in 5 volumes of acetone.

The obtained compound, deacyl-deacetyl-$GM_2$ (N,N'-dilyso $GM_2$), is high-vacuum dried and again dissolved in 1 ml of dimethylformamide.

30 mg of 9-fluorenylmethyloxycarbonyl-N-hydroxysuccinimide dissolved in 0.5 ml tetrahydrofurane are slowly added, and the reaction lasts 1 hour at room temperature. Once the reaction is achieved, add 50 µl of acetic anhydride and react for 30 min. Supplement with 150 µl of pyridine in order to remove the protective compound, react for 18 hours at room temperature, precipitate in 10 volumes of acetone and dry.

The obtained compound is then dissolved in $Na_2CO_3$ 1M and kept for 1 hour at 60° C. Dialyze, concentrate to 0.5 ml and precipitate in 5 volumes of acetone.

The compound is then passed a through S-Sepharose column (H+ form) balanced in methanol. Wash with methanol and dissolve N-lyso-$GM_2$ with $NH_4Cl$ 10 nM in methanol. The compound is dried, again water-dissolved, brought to pH 10 with NaOH 0.01N, again dialyzed and then lyophilized.

20 mg of sulfur trioxide-pyridine complex are then added and the reaction lasts 15 min at room temperature. Once the reaction is achieved, dialyze in water, concentrate at 0.5 ml and precipitate in 10 volumes of acetone.

Obtained compound: 48 mg

Chromatographed on silica-gel plate with chloroform/methanol/$CaCl_2$ 0.3% 60/35/8, it proves to be a unitary compound with Rf=0.18 ($GM_2$=0.52).

EXAMPLE 3

N-SULFO-LYSO $GM_3$ 100 mg (0.084 mM) of $GM_3$ are dissolved in 2 ml KOH 3M and the reaction lasts 60 hours at 90° C. Once the reaction is achieved, cool and bring to pH 6.5 with hydrochloric acid. Keep for 18 hours at 4° C. and then filtrate the separate fatty acids. Dialyze against $H_2O$, concentrate and precipitate in 5 volumes of acetone.

The compound obtained, deacyl-deacetyl-$GM_3$(N,N'-dilyso $GM_3$), is high-vacuum dried and again dissolved in 1 ml of dimethylformamide.

30 mg of 9-fluorenylmethyloxycarbonyl-N-hydroxysuccinimide dissolved in 0.5 ml tetrahydrofurane are slowly added and reacted for 1 hour at room temperature. At the end, supplement with 50 µl of acetic anhydride and react for 30 min. Then 150 µl of piperidine are added in order to remove the protective compound; react for 18 hours at room temperature, precipitate in 10 volumes of acetone and dry.

The obtained compound is then dissolved in $Na_2CO_3$ 1M and kept at 60° C. for 1 hour. Dialyze, concentrate to 0.5 ml and precipitate in 5 volumes of acetone.

The compound is then passed through a S-Sepharose column (H+ form) balanced in methanol. Wash with methanol and then dissolve deacyl-$GM_3$(N-lyso $GM_3$) with $NH_4Cl$ 10 nM in methanol. The compound is dried, again water-dissolved, brought to pH 10 with NaOH 0.01N, again dialyzed and then lyophilized.

Add 20 mg of sulfur trioxide-pyridine complex and react for 15 min at room temperature. Once the reaction is achieved, dialyze against $H_2O$, concentrate at 0.5 ml and precipitate in 10 volumes of acetone.

Obtained compound: 45 mg

Chromatographed on silica-gel plate with chloroform/methanol/$CaCl_2$ 0.3% 60/35/8, it proves to be a unitary compound with Rf=0.23 ($GM_3$=0.67).

EXAMPLE 4

N'-SULFO-$GM_1$ 500 mg (0.33 mM) of deacetyl $GM_1$ (N'-lyso $GM_1$) are dissolved in 50 ml $Na_2CO_3$ 0.2M in $H_2O$. 210.1 mg (1.32 mM) of sulfur trioxide/pyridine complex are added and reacted for 15 min at room temperature. Once the reaction is achieved, dialyze against $H_2O$, concentrate at 100 mg/ml and precipitate in 10 volumes of acetone.

Obtained compound: 460 mg (86% theoretical)

Chromatographed on silica-gel plate with chloroform/methanol./$CaCl_2$ 0.3% 60/35/8. it proves to be a unitary compound with Rf=0.18 ($GM_1$=0.40, N'-deacetyl $GM_1$= 0.20).

EXAMPLE 5

N-SULFO-LYSO $GD_{1a}$ 500 mg (0.26 mM) of $GD_{1a}$ are dissolved in 10 ml KOH 3M and the reaction lasts 60 hours at 90° C. Once the reaction is achieved, cool and bring to pH 6.5 with hydrochloric acid. Keep for 18 hours at 4° C. and then filtrate the separated fatty acids. Dialyze against $H_2O$, concentrate and precipitate in 5 volumes of acetone.

The compound obtained, deacyl-deacetyl-$GD_{1a}$(N,N'-dilyso $GD_{1a}$), is high-vacuum dried and again dissolved in 5 ml of dimethylformamide.

150 mg of 9-fluorenylmethyloxycarbonyl-N-hydroxysuccinimide dissolved in 2.5 ml tetrahydrofurane are slowly added and reacted for 1 hour at room temperature. At the end, supplement with 0.5 ml of acetic anhydride and react for 30 min. One ml of piperidine is then added in order to remove the protective compound, react for 18 hours at room temperature, precipitate in 10 volumes of acetone and dry.

The obtained compound is then dissolved in $Na_2CO_3$ 1M and kept at 60° C. for 1 hour. Dialyze, concentrate at 2.5 ml and precipitate in 5 volumes of acetone.

The compound is passed through a S-Sepharose column (H+ form) balanced in methanol. Wash with methanol and then dissolve deacyl$GD_{1a}$ with $NH_4Cl$ 10 nM in methanol. The compound is dried, again water-dissolved, brought to pH 10 with NaOH 0.01N, again dialyzed and then lyophilized.

20 mg of the sulfur trioxide/pyridine complex are added and reacted for 15 min at room temperature. Once the reaction is achieved, dialyze against $H_2O$, concentrate at 0.5 ml and precipitate in 10 volumes of acetone.

Obtained compound: 225 mg

Chromatographed on silica-gel plate with chloroform/methanol/$CaCl_2$ 0.3% 60/35/8. it proves to be a unitary compound with Rf=0.12 ($GD_{1a}$=0.37).

EXAMPLE 6

N,N'-DISULFO-N,N'-DILYSO $GM_1$ 250 mg (0.20 mM) of N,N'-dilyso $GM_1$ are dissolved in 5 ml $Na_2CO_3$ 0.2M, then add 300 mg of the sulfur trioxide/pyridine complex and react at room temperature.

At the end, dialyze against $H_2O$, concentrate at 100 mg and precipitate in 10 volumes of acetone.

Chromatograph on silica-gel plate with chloroform/methanol/$H_2O$ 60/30/6, collect pure fractions, concentrate and again precipitate in acetone.

Obtained compound: 110 mg

Chromatographed on silica-gel plate with chloroform/methanol/$CaCl_2$ 0.3% 60/35/8. it proves to be a unitary compound with Rf=0.13 (N,N'-dilyso-$GM_1$=0.29).

EXAMPLE 7

N'-SULFO-$GM_3$ 100 mg (0.084 mM) of $GM_3$ are dissolved in 10 ml NaOH 1N and react for 15 hours at 90° C. Once the reaction is achieved, neutralize with HCl 1N and partition with 5 volumes of chloroform/methanol 2/1.

Dry the organic phase with 15 ml of $Na_2CO_3$ 0.2 M and react with 200 mg of sulfur trioxide/pyridine complex (sulfonating agent/ganglioside ratio: 2/1) for 3 hours at room temperature.

Concentrate and dialyze against distilled $H_2O$. Dry and chromatograph on silica-gel plate with chloroform/methanol/$NH_3$ 5N 60/25/4.

Obtained compound: 70 mg

Chromatographed on silica-gel plate with chloroform/methanol/$NH_3$ 5N 60/35/8. it proves to be a unitary compound with Rf=0.56 ($GM_3$0.67, deacetyl-$GM_3$=0.48).

EXAMPLE 8

N-ACETYL,N'-SULFO-DILYSO $GM_1$ 500 mg (0.37 mM) of N-acetyl-N,N'-dilyso $GM_1$ are dissolved in 20 ml of $Na_2CO_3$ 0.2 M; react with 250 mg of sulfur trioxide/pyridine complex (sulfonating agent/ganglioside ratio: 20/1) for 3 hours at room temperature.

Concentrate and dialyze against distilled $H_2O$. Dry and chromatograph on silica-gel plate with chloroform/methanol/$NH_3$ 5N 60/35/8.

Obtained compound: 325 mg

Chromatographed on silica-gel plate with chloroform/methanol/$NH_3$ 5N 60/35/8., it proves to be a unitary compound with Rf=0.58 (de-N'acetyl,N-acetyl-dilyso $GM_1$= 0.28).

EXAMPLE 9

N-4-CHLOROBENZENESULFONYL-LYSO $GM_1$ 500 mg (0.39 mM) of N-lyso $GM_1$ are dissolved in 25 ml dimethylformamide. Supplement with 2 ml (14.4 mM) of triethylamine and then 1.6 g (7.58 mM) of 4-chloro benzenesulfonyl chloride.

React at room temperature for 24 hours. Add 1 g sodium acetate and dry by means of a rotating evaporator, re-suspend with sodium carbonate 1N and saponify for 18 hours at 70° C.

The resulting raw compound is dialyzed against $H_2O$, dried and purified by means of silica gel chromatography with chloroform/methanol/ammonium carbonate 3.2% in water, 60/25/4.

Collect pure fractions, dry, re-suspend with sodium carbonate 1N, dialyze against distilled $H_2O$ and then precipitate in 100 ml acetone.

Obtained compound: 120 mg

Chromatographed on silica-gel plate with chloroform/methanol/$CaCl_2$ 0.3% 60/35/8. it proves to be a unitary compound with Rf=0.30 ($GM_1$=0.40, N-deacyl-lyso $GM_1$= 0.17).

EXAMPLE 10

N-BENZENESULFONYL-LYSO $GM_1$ 500 mg (0.39 mM) of N-lyso $GM_1$ are dissolved in 10 ml dimethylformamide. Take solution to 0° C. Supplement with 0.118 ml (0.84 mM) of triethylamine and then 0.106 g (0.83 mM) of benzenesulfonylchloride.

React at room temperature for 24 hours at 0° C.

Add 1 g sodium acetate and dry by means of a rotating evaporator.

The resulting raw compound is dialyzed against $H_2O$, dried and purified by means of silica gel chromatography with chloroform/methanol/ammonium carbonate 3.2% in water 60/25/4.

Pure fractions are collected, dried, re-suspended with sodium carbonate 1N, dialyzed against distilled $H_2O$ and then precipitated in 100 ml acetone.

Obtained compound: 150 mg

Chromatographed on silica-gel plate with chloroform/methanol/$CaCl_2$ 0.3% 60/35/8, it proves to be a unitary compound with Rf=0.30 ($GM_1$ =0.40, N-deacyl-lyso $GM_1$= 0.17).

EXAMPLE 11

N-METHANESULFONYL-LYSO $GM_1$ 500 mg (0.39 mM) of N-lyso $GM_1$ are dissolved in 10 ml dimethylformamide. Supplement with 112 ml (0.76 mM) of methansulfonylimidazole.

React at room temperature for 72 hours. Add 1 g sodium acetate and dry by means of a rotating evaporator, resuspend with sodium carbonate 1N and saponify for 18 hours at 70° C.

The resulting raw compound is dialyzed against $H_2O$, dried and purified by means of silica gel chromatography with chloroform/methanol/ammonium carbonate 3.2% in water 60/25/4.

Pure fractions are collected, dried, re-suspended with sodium carbonate 1N, dialyzed against distilled $H_2O$ and then precipitated in 100 ml acetone.

Obtained compound: 100 mg

Chromatographed on silica-gel plate with chloroform/methanol/$CaCl_2$ 0.3% 60/35/8, it proves to be a unitary compound with Rf=0.20 ($GM_1$=0.40, N-deacyl-lyso $GM_1$= 0.17).

EXAMPLE 12

N-2-BROMOETHANESULFONYL-LYSO $GM_1$ 500 mg (0.39 mM) of N-deacyl-lyso $GM_1$ are dissolved in 10 ml dimethylformamide. Supplement with 316 µl (2.2 mM) of triethylamine, 160 mg (0.76 mM) of the 2-bromoethanesulfonic acid sodium salt and 194 mg (0.76 mM) of chloromethylpyridine iodide.

React at room temperature for 72 hours.

Add 1 g sodium acetate and dry the compound by means of a rotating evaporator, re-suspend with sodium carbonate 1N and saponify for 18 hours at 70° C.

The resulting raw compound is dialyzed against $H_2O$, dried and purified by means of silica gel chromatography with chloroform/methanol/ammonium carbonate 3.2% in water 60/25/4.

Pure fractions are collected, dried, re-suspended with sodium carbonate 1N, dialyzed against distilled $H_2O$ and then precipitated in 100 ml acetone.

Obtained compound: 126 mg

Chromatographed on silica-gel plate with chloroform/methanol/$CaCl_2$ 0.3% 60/35/8, it proves to be a unitary compound with Rf=0.22 ($GM_1$=0.40, N-deacyl-lyso $GM_1$= 0.17, N'-deacetyl-lyso $GM_1$ 0.20).

EXAMPLE 13

N-HEXADECANESULFONYL-LYSO $GM_1$ 500 mg (0.38 mM) of N-lyso $GM_1$ are dissolved in 2.5 ml dimethylformamide. Add at room temperature 316 µl (2.28 mM) of triethylamine, 7 mg (0.83 mM) of hexadecanesulfonic acid sodium salt and 194.2 mg (0.76 mM) of chloromethylpyridine iodide dissolved in 2.5 ml dimethylformamide.

React at room temperature for 18 hours.

Precipitate in 100 ml acetone. Filtrate and dry. Purify by means of silica gel chromatography with chloroform/methanol/$H_2O$ 60/30/6.

Pure fractions are collected, dried, re-suspended with $Na_2C_3$ 1N, dialyzed against distilled $H_2O$, concentrated at 5 ml and precipitated in 100 ml acetone.

Obtained compound: 2,05 mg

Chromatographed on silica-gel plate with chloroform/methanol/$CaCl_2$ 0.3% 60/35/8, it proves to be a unitary compound with Rf=0.38 ($GM_1$=0.40, N-deacyl-lyso $GM_1$= 0.17).

EXAMPLE 14

N-PYRIDINESULFONYL-LYSO $GM_1$ 500 mg (0.38 mM) of N-lyso $GM_1$ are dissolved in 2.5 ml dimethylformamide. Add at room temperature 316 µl (2.28 mM) of triethylamine, 132 mg (0.83 mM) of pyridinesulfonic acid and 194.2 mg (0.76 mM) of chloromethylpyridine iodide dissolved in 2.5 ml dimethylformamide.

React at room temperature for 18 hours.

Precipitate in 100 ml acetone. Filtrate and dry. Purify by means of silica gel chromatography with chloroform/methanol/$H_2O$ 60/30/6.

Pure fractions are collected, dried, re-suspended with $Na_2CO_3$ 1N, dialyzed against distilled $H_2O$, then concentrated at 5 ml and precipitated in 50 ml acetone.

Obtained compound: 240 mg

Chromatographed on silica-gel plate with chloroform/methanol/$CaCl_2$ 0.3% 60/35/8, it proves to be a unitary compound with Rf=0.35 ($GM_1$=0.43, N-deacyl-lyso $GM_1$= 0.24) and plate-fluorescent at 254 nm.

EXAMPLE 15

N-O-SULFO-LYSO $GM_1$ 500 mg (0.36 mM) of N-sulfo-lyso $GM_1$ are dissolved in 5 ml dimethylformamide. Add at room temperature 0.5 ml (3.6 mM) of triethylamine, and 276 mg (1.8 mM) of the sulfur trioxide/dimethylformamide complex.

React under stirring at room temperature for 5 hours. Precipitate in 10 ml acetone. Dissolve the resulting raw compound in 50 ml $Na_2CO_3$ 1%, dialyze against $H_2O$ and lyophilize.

Obtained compound: 650 mg

Chromatographed on silica-gel plate with chloroform/methanol/$CaCl_2$ 0.3% 60/35/8, it shows a Rf ranging from 0.09 to 0.15. Molar ratio of sulfate groups/neuraminic acid 5/1 (determination of sulfate groups by means of ion chromatography and determination of the neuraminic acid by means of the resorcinol method). Specific absorption I.R. S=O groups: 120 $cm^{-1}$ (KRb).

EXAMPLE 16

N'-O-SULFO-LYSO $GM_1$ 500 mg (0.31 nM) of N'-sulfo-lyso $GM_1$ are dissolved in 5 ml anhydrous dimethylformamide. Add at room temperature 0.43 ml (3.1 mM) of triethylamine, and 237 mg (1.55 mM) of the sulfur trioxide/dimethylformamide complex.

React under stirring at room temperature for 5 hours and precipitate in 5 volumes of acetone.

Dissolve the resulting raw compound in 50 ml $Na_2CO_3$ 1%, dialyze against $H_2O$ and lyophilize.

Obtained compound: 620 mg

Chromatographed on silica-gel plate with chloroform/methanol/$CaCl_2$ 0.3% 60/35/8, it shows a Rf ranging from 0.01 to 0.05. Molar ratio of the sulfate groups/neuraminic acid 5/1 (determination of sulfate groups by means of ion chromatography and determination of the neuraminic acid using the resorcinol method). Specific absorption I.R. S=O groups: 1260 $cm^{-1}$ (KRb).

EXAMPLE 17

INJECTABLE PHARMACEUTICAL PREPARATIONS

Preparation No. 1
One 2-ml vial contains:
Active ingredient 5 mg
Sodium chloride 16 mg
Citrate buffer pH=6
In water for injection, q.s. to 2 ml Preparation No. 2
One 2-ml vial contains:
Active ingredient 50 mg
Sodium chloride 16 mg
Citrate buffer pH=6
In water for injection, q.s. to 2 ml Preparation No. 3
One 4-ml vial contains:
Active ingredient 100 mg
Sodium chloride 32 mg
Citrate buffer pH =6
In water for injection, q.s. to 4 ml

EXAMPLE 18

PHARMACEUTICAL PREPARATIONS IN 2 VIALS

These preparations are prepared with 2 vials. The first vial contains the active ingredient in the form of a lyophilized powder in quantities varying from 10% to 90% in weight, together with a pharmaceutically acceptable excipient, such a glycine or mannitol. The second vial contains a solvent, such as sodium chloride and a citrate buffer.

The contents of both ampules are mixed up immediately before administration and the lyophilized active ingredient is rapidly dissolved, thus resulting in an injectable solution.

Method No. 1
a. One 2-ml vial of lyophilized powder contains:
Active ingredient 5 mg
Glycine 30 mg
b. One 2-ml vial of solvent contains:
Sodium chloride 16 mg
Citrate buffer 2 mg
In water for injection, q.s. to 2 ml Method No. 2
a. One 3-ml vial of lyophilized powder contains:
Active ingredient 5 mg
Mannitol 40 mg
b. One 2-ml vial of solvent contains:
Sodium chloride 16 mg
Citrate buffer
In water for injection, q.s. to 2 ml Method No. 3
a. One 3-ml vial of lyophilized powder contains:
Active ingredient 50 mg
Glycine 25 mg
b. One 3-ml vial of solvent contains:
Sodium chloride 24 mg
Citrate buffer
In water for injection, q.s. to 3 ml Method No. 4
a. One 3-ml vial of lyophilized powder contains:
Active ingredient 50 mg
Mannitol 20 mg
b. One 3-ml vial of solvent contains:
Sodium chloride 24 mg
Citrate buffer
In water for injection, q.s. to 3 ml Method No. 5
a. One 5-ml vial of lyophilized powder contains:
Active ingredient 150 mg
Glycine 50 mg
b. One 4-ml vial of solvent contains:
Sodium chloride 32 mg
Citrate buffer
In water for injection, q.s. to 4 ml Method No. 6
a. One 5-ml vial of lyophilized powder contains:
Active ingredient 100 mg
Mannitol 40 mg
b. One 4-mi vial of solvent contains:
Sodium chloride 32 mg
Citrate buffer
In water for injection, q.s. to 4 ml Method No. 7
a. One 3-ml vial of lyophilized powder contains:
Active ingredient
micronized, sterile 40 mg
b. One 3-ml vial of solvent contains:
Tween 80® 10 mg
Sodium chloride 24 mg
Phosphate buffer
In water for injection, q.s. to 3 ml Method No. 8
a. One 5-ml vial of lyophilized powder contains:
Active ingredient
Micronized, sterile 100 mg
b. One 4-ml vial of solvent contains:
Tween 80® 15 mg
Soybean lecithin 5 mg
Sodium chloride 36 mg
Citrate buffer
In water for injection, q.s. to 4 ml

EXAMPLE 19

PHARMACEUTICAL PREPARATIONS FOR TRANSDERMAL ADMINISTRATION

Preparation No. 1.
A bandage contains:
Active ingredient 100 mg

Glycerol 1.6 g
Polyvinyl alcohol 200 mg
Polyvinyl pyrrolidone 100 mg
Excipient to increase
Transdermal penetration 20 mg
Water 1.5 g
Preparation No. 2.
  100 g ointment contain:
  Active ingredient 4.0 g
  (in 5 g phospholipid liposomes)
  Polyethylene glycol monostearate 1.5 g
  Glycerol 1.5 g
  Beta-oxybenzoic acid ester 125 mg
  Water 72.9 g

EXAMPLE 20

PHARMACEUTICAL PREPARATIONS FOR ORAL ADMINISTRATION

Preparation No. 1.
  A tablet contains:
  Active ingredient 20 mg
  Single-crystal cellulose 150 mg
  Lactose 20 mg
  Starch 10 mg
  Magnesium stearate 5 mg
Preparation No. 2.
  A pill contains:
  Active ingredient 30 mg
  Carboxymethyl cellulose 150 mg
  Starch 15 mg
  Lactose 10 mg
  Sucrose 35 mg
  Coloring agent 0.5 mg
Preparation No. 3.
  A gelatine capsule contains:
  Active ingredient 40 mg
  Lactose 100 mg
  Gastroresistant covering 5 mg
Preparation No. 4.
  A soft gelatine capsule contains:
  Active ingredient 50 mg
  Vegetable oil 200 mg
  Beeswax 20 mg
  Gelatine 150 mg
  Glycerol 50 mg
  Coloring agent 3 mg This invention being thus described, it is obvious that these methods can be modified in various ways. Such modifications are not to be considered as divergences from the very spirit and purpose of the invention, and any modification that would appear evident to an expert in the field comes within the scope of the following claims:

We claim:

1. Semisynthetic ganglioside analogues, having a sialic acid residue portion and oligosaccharide hydroxyl groups, selected from the group consisting of N-sulfo-, N-hydrocarbyl-sulfonyl- and N-hydrocarbyloxy-sulfonyl-N,N'-dilyso-gangliosides and N'-acyl derivatives thereof, N'-sulfo-, N'hydrocarbyl-sulfonyl- and N'-hydrocarbyloxy-sulfonyl-N,N'-dilyso-gangliosides and N-acyl derivatives thereof; N,N'-di or polysulfo-N,N'-di-or poly-lyso-gangliosides, N,N'-di or polyhydrocarbylsulfonyl-N,N'-di- or poly-lyso-gangliosides and N,N'-di- or polyhydrocarbyloxy-N,N'-di- or poly-lyso-gangliosides; salts of said ganglioside analogues; esters and amides of the carboxyl groups of the sialic acid residue portion of said ganglioside analogues; inner esters of the sialic acid carboxyl groups and the oligosaccharide hydroxyl groups of said ganglioside analogues; and organic or sulfonic acid esters of the hydroxyl groups of said ganglioside analogues.

2. Ganglioside analogues according to claim 1, wherein the hydrocarbyl radical is selected from the group consisting of alkyl with up to 24 carbon atoms, aryl with up to 24 carbon atoms, aralkyl with up to 24 carbon atoms, and cycloalkyl with up to 24 carbon atoms.

3. Ganglioside analogues according to claim 2, wherein hydrocarbyl is an alkyl radical with a maximum of 24 carbon atoms.

4. Ganglioside analogues according to claim 3, wherein the alkyl radical is substituted with functions selected from the group consisting of hydroxyl, amino and halogen.

5. Ganglioside analogues according to claim 4, wherein the alkyl radical is interrupted in the carbon atom chain by heteroatoms.

6. Ganglioside analogues according to claim 3, wherein the alkyl radical has a maximum of 6 carbon atoms.

7. Ganglioside analogues according to claim 3, wherein the alkyl radical is saturated or unsaturated and has between 14 and 22 carbon atoms.

8. Ganglioside analogues according to claim 2, wherein the aryl radical has a maximum of 12 carbon atoms.

9. Ganglioside analogues according to claim 8, wherein the aryl radical is an unsubstituted phenyl group or a phenyl group substituted with 1 to 3 $C_{1-4}$ alkyl groups.

10. Ganglioside analogues according to claim 2, wherein the aralkyl radical has a maximum of 12 carbon atoms.

11. Ganglioside analogues according to claim 10, wherein the aralkyl radical is formed by a $C_{2-4}$ alkylene group and an aromatic portion formed by a phenyl group unsubstituted or substituted with 1 to 3 $C_{1-4}$ alkyl groups or $C_{1-4}$ alkoxy groups.

12. Ganglioside analogues according to claim 2, wherein the cycloalkyl radical is selected from the group consisting of cyclopropyl, cyclohexyl, cyclobutyl, and cyclopentyl, wherein said cycloalkyl radical may be optionally substituted with $C_{1-4}$ alkyl groups.

13. Ganglioside analogues according to claim 1 excluding N'-acyl derivatives and N-acyl derivatives.

14. Ganglioside analogues according to claim 1, wherein the acyl group on the sphingosine N or on the neuraminic N' is from an aliphatic acid with a maximum of 24 carbon atoms.

15. Ganglioside analogues according to claim 14, wherein the acyl group is substituted with a polar unit selected from the group consisting of halogens, free or esterified hydroxy-L groups, and free or esterified mercaptan groups.

16. Ganglioside analogues according to claim 1, wherein the acyl group on the sphingosine N or on the neuraminic N' is from benzoic acid or a benzoic acid homoloque where the phenyl group is substituted with 1 to 3 substituents selected from the group consisting of $C_{1-4}$ alkyl, $C_{1-4}$ alkoxyl, amino, $C_{1-4}$-alkylamino and di($C_{1-4}$alkyl)amino.

17. Ganglioside analogues according to claim 1, wherein the acyl group on the sphingosine N or on the neuraminic N' is from an araliphatic acid with a $C_{2-4}$ aliphatic-alkylene chain and an aromatic portion wherein the phenyl group is substituted with 1–3 substituents selected from the group

31 consisting of $C_{1-4}$ alkyl, $C_{1-4}$ alkoxy, amino, $C_{1-4}$ alkylamino and di($C_{1-4}$ alkyl)amino.

18. Ganglioside analogues according to claim 1, wherein the acyl group on the sphingosine N or on the neuraminic N' is from cyclopropane, cyclobutane, cyclopentane or cyclohexane carboxylic acid.

19. Ganglioside analogues according to claim 1, wherein the acyl group on the sphingosine N or on the neuraminic N' is from a heterocyclic acid with a single heterocyclic ring, wherein said heterocyclic ring contains a single heteroatom selected from the group consisting of O, N and S and wherein said heterocyclic ring is of either aromatic or aliphatic nature.

20. Ganglioside analogues according to claim 1 which are carboxyl esters from an aliphatic alcohol with a maximum of 12 carbon atoms, or from an araliphatic alcohol with a benzene ring unsubstituted or substituted with 1 to 3 $C_{1-4}$ alkyl groups, and having a maximum of 4 carbon atoms in the aliphatic portion of the araliphatic alcohol.

21. Ganglioside analogues according to claim 1 which are carboxyl amides from ammonium or an aliphatic amine with a maximum of 12 carbon atoms.

22. Ganglioside analogues according to claim 1 esterified with sulfonic acid.

23. Ganglioside analogues according to claim 1 in the form of a mixture, wherein a first analogue is esterified with sulfuric acid forming an esterified hydroxyl, and wherein a second analogue is not esterified with sulfuric acid.

24. The functional derivative according to claim 22 which is a total ester.

25. Ganglioside analogues according to claim 1 esterified with an organic acid.

26. Ganglioside analogues according to claim 25, in which the ester is a peracylated moiety wherein the acyl group is from an aliphatic acid with a maximum of 24 carbon atoms or from an araliphatic acid in which the aliphatic moiety is a $C_{2-4}$ alkylene group and the phenyl moiety is optionally substituted with 1 to 3 methyl or methoxyl groups.

27. A compound selected from the group consisting of:

N-ethyl-sulfonyl-N'-acetyl-N,N'-dilyso-$GM_1$,

N-propyl-sulfonyl-N'-acetyl-N,N'-dilyso-$GM_1$,

N-n-butyl-sulfonyl-N'-acetyl-N,N'-dilyso-$GM_1$,

N-n-pentyl-sulfonyl-N'-acetyl-N,N'-dilyso-$GM_1$,

N-n-hexyl-sulfonyl-N'-acetyl-N,N'-dilyso-$GM_1$,

N-n-heptyl-sulfonyl-N'-acetyl-N,N'-dilyso-$GM_1$,

N-n-octyl-sulfonyl-N'-acetyl-N,N'-dilyso-$GM_1$,

N-n-decyl-sulfonyl-N'-acetyl- N,N'-dilyso- $GM_1$,

N-2-bromoethyl-sulfonyl-N'-acetyl-N,N'-dilyso-$GM_1$,

N-hexadecyl-sulfonyl-N'-acetyl-N,N'-dilyso-$GM_1$,

N-3-chloropropyl-sulfonyl-N'-acetyl-N,N'-dilyso-$GM_1$,

N-6-bromohexyl-sulfonyl-N'-acetyl-N,N'-dilyso-$GM_1$,

N-benzyl-sulfonyl-N'-acetyl-N,N'-dilyso-$GM_1$,

N-4-chlorobenzyl-sulfonyl-N'-acetyl-N,N'-dilyso-$GM_1$,

N-4-aminobenzyl-sulfonyl-N'-acetyl-N,N'-dilyso-$GM_1$,

N-3,4,5-trimethoxybenzyl-sulfonyl-N'-acetyl-N,N'-dilyso-$GM_1$, and

N-sulfo-N'-acetyl-N,N'-dilyso-$GM_1$.

28. A compound selected from the group consisting of N'-sulfo-N'-lyso-$GM_1$ and esters thereof, wherein said esters are from alcohols selected from the group consisting of ethyl alcohol, propyl alcohol, n-butyl alcohol, n-pentyl alcohol, n-hexyl alcohol, n-heptyl alcohol, n-octyl alcohol, n-decyl alcohol, 2-bromoethyl alcohol, hexadecyl alcohol, 3-chloropropyl alcohol, 6-bromohexyl alcohol, benzylsulfonyl alcohol, 4-chlorobenzyl alcohol, 4-aminobenzyl alcohol, and 3,4,5-trimethoxy-benzyl alcohol.

29. A compound selected from the group consisting of N,N'-di-sulfo-N,N'-di-lyso-$GM_1$ and esters thereof, wherein said esters are from alcohols selected from the group consisting of ethyl alcohol, propyl alcohol, n-butyl alcohol, n-pentyl alcohol, n-hexyl alcohol, n-heptyl alcohol, n-octyl alcohol, n-decyl alcohol, 2-bromoethyl alcohol, hexadecyl alcohol, 3-chloropropyl alcohol, 6-bromohexyl alcohol, benzyl-sulfonyl alcohol, 4-chlorobenzyl alcohol, 4-aminobenzyl alcohol, and 3,4,5-trimethoxybenzyl alcohol.

30. A compound selected from the group consisting of: N-ethyl-sulfonyl-N'-acyl-N,N'-dilyso-$GM_1$, N-propyl sulfonyl-N'-acyl-N,N'-dilyso-$GM_1$, N-n-butyl-sulfonyl-N'-acyl-N,N'-dilyso-$GM_1$, N-n-pentyl-sulfonyl-N'-acyl-N,N'-dilyso-$GM_1$, N-n-hexyl-sulfonyl-N'-acyl-N,N'-dilyso-$GM_1$, N-n-octyl-sulfonyl-N'-acyl-N,N'-dilyso-$GM_1$, N-n-decyl-sulfonyl-N'-acyl-N,N'-dilyso-$GM_1$, N-2-bromoethyl-sulfonyl-N'-acyl-N,N'-dilyso-$GM_1$, N-hexadecyl-sulfonyl-N'-acyl-N,N'-dilyso-$GM_1$, N-3-chloropropyl-sulfonyl-N'-acyl-N,N'-dilyso-$GM_1$, N-6-bromohexyl-sulfonyl-N'-acyl-N,N'-dilyso-$GM_1$, N-benzyl-sulfonyl-N'-acyl-N,N'-dilyso-$GM_1$, N-4-chlorobenzyl-sulfonyl-N'-acyl-N,N'-dilyso-$GM_1$, N-4-aminobenzyl-sulfonyl-N'-acyl-N,N'-dilyso-$GM_1$, N-3,4,5-trimethoxybenzyl-sulfonyl-N'-acyl-N,N'-dilyso-$GM_1$, N-acyl-N'-ethyl-sulfonyl-N,N'-dilyso-$GM_1$, N-acyl-N'-propyl sulfonyl-N,N'-dilyso-$GM_1$, N-acyl-N'-n-butyl-sulfonyl-N,N'-dilyso-$GM_1$, N-acyl-N'-pentyl-sulfonyl-N,N'-dilyso-$GM_1$, N-acyl-N'-n-hexyl-sulfonyl-N,N'-dilyso-$GM_1$, N-acyl-N'-n-heptyl-sulfonyl-N,N'-dilyso-$GM_1$, N-acyl-N'-n-octyl-sulfonyl-N,N'-dilyso-$GM_1$, N-acyl-N'-n-decyl-sulfonyl-N,N'-dilyso-$GM_1$, N-acyl-N'-2-bromoethyl-sulfonyl-N,N'-dilyso-$GM_1$, N-acyl-N'-hexadecyl-sulfonyl-N,N'-dilyso-$GM_1$, N-acyl-N'-3-chloropropyl-sulfonyl-N,N'-dilyso-$GM_1$, N-acyl-N'-6-bromohexyl-sulfonyl-N,N'-dilyso-$GM1$, N-acyl-N'-benzyl-sulfonyl-N,N'-dilyso-$CM_1$, N-acyl-N-4-aminobenzyl-sulfonyl-N,N'-dilyso-$GM_1$, and N-acyl-N'-3,4,5-trimethoxybenzyl-sulfonyl-N,N'-dilyso-$GM_1$, wherein the acyl group is from an acid selected from the group consisting of acetic, chloroacetic, dichloroacetic, propionic, valeric, trimethyl-acetic acid, caproic acid, and capric acid.

31. Pharmacologically acceptable salts of any one of the analogues as claimed in claim 1, wherein the cation of the salt is a metallic or basic cation.

32. The salt according to claim 31 which is a sodium salt.

33. Pharmaceutical compositions comprising at least one compound according to claim 1 and a pharmaceutically acceptable excipient, for use in therapy.

34. A method of reducing glutamate-induced neurotoxicity which comprises administering to a patient in need thereof a pharmaceutical composition according to claim 33.

35. A method for inhibiting expression of $CD_4$ determinants present on the surface of human cells which comprises administering to said cells a pharmaceutical composition according to claim 33.

36. A process for the preparation of ganglioside analogues according to claim 1, which comprises treating a N,N'-dilyso-ganglioside or a derivative or a salt thereof with sulfuric acid, a hydrocarbyloxy-sulfuric acid or a hydrocarbyl-sulfonic acid, or a derivative thereof, optionally acylating an amino group in position N- or N'-, and in the resulting acylated amino groups optionally hydrolyzing one of the two acylated amino groups into free amino groups, optionally converting free carboxyl groups or free hydroxyl groups into their functional derivatives, and optionally converting obtained compounds into corresponding metal, organic base or acid salts.

37. Compounds with the following formula:

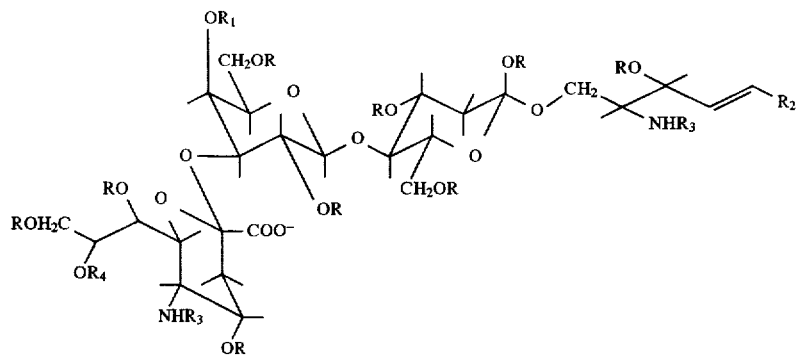
wherein:
R=H or $SO_3H$;
$R_1$=H,
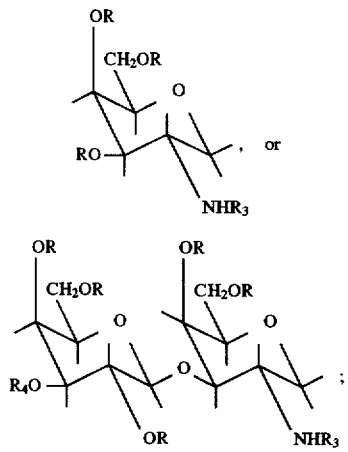
$R_2$=—$(CH_2)_n$—$CH_3$, wherein n=12–14;
$R_3$=H, acyl or $SO_2R_5$, provided that at least one $R_3$ is $SO_2R_5$,
$R_4$=H, or
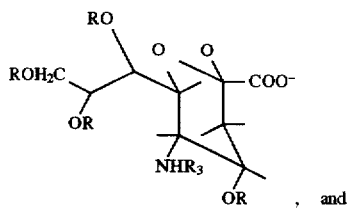
, and
$R_5$=alkyl, aryl or OX, wherein X=H, alkyl or aryl.
* * * * *